United States Patent
Bar-Even et al.

(10) Patent No.: US 10,377,994 B2
(45) Date of Patent: *Aug. 13, 2019

(54) USE OF THE REDUCTIVE GLYCINE PATHWAY FOR GENERATING FORMATOTROPHIC AND AUTOTROPHIC MICROORGANISMS

(71) Applicant: Yeda Research and Development Co. Ltd., Rehovot (IL)

(72) Inventors: Arren Bar-Even, Tel-Aviv (IL); Ron Milo, Kfar-Saba (IL); Elad Noor, Rehovot (IL); Oren Yishai, Rehovot (IL)

(73) Assignee: Yeda Research and Developmetn Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/162,427

(22) Filed: Oct. 17, 2018

(65) Prior Publication Data

US 2019/0032027 A1 Jan. 31, 2019

Related U.S. Application Data

(63) Continuation of application No. 14/417,559, filed as application No. PCT/IL2013/050643 on Jul. 29, 2013, now Pat. No. 10,155,933.

(60) Provisional application No. 61/676,962, filed on Jul. 29, 2012.

(51) Int. Cl.
| | |
|---|---|
| *C12N 9/88* | (2006.01) |
| *C12N 9/04* | (2006.01) |
| *C12N 15/52* | (2006.01) |
| *C12P 7/64* | (2006.01) |
| *C12N 9/02* | (2006.01) |
| *C12N 9/00* | (2006.01) |
| *C12P 7/40* | (2006.01) |
| *C12M 1/42* | (2006.01) |
| *C12N 9/06* | (2006.01) |
| *C12N 9/78* | (2006.01) |
| *C12N 13/00* | (2006.01) |

(52) U.S. Cl.
CPC .......... *C12N 9/0008* (2013.01); *C12M 35/02* (2013.01); *C12N 9/0028* (2013.01); *C12N 9/78* (2013.01); *C12N 9/93* (2013.01); *C12N 13/00* (2013.01); *C12N 15/52* (2013.01); *C12P 7/40* (2013.01); *C12Y 102/01002* (2013.01); *C12Y 105/01005* (2013.01); *C12Y 105/01015* (2013.01); *C12Y 305/04009* (2013.01); *C12Y 603/04003* (2013.01)

(58) Field of Classification Search
CPC . C12N 9/02; C12N 9/00; C12N 15/52; C12N 9/06; C12N 9/78; C12P 7/40; C12M 1/42
See application file for complete search history.

(56) References Cited

U.S. PATENT DOCUMENTS

| | | | |
|---|---|---|---|
| 2009/0203070 A1* | 8/2009 | Devroe | C12N 9/1007 435/69.1 |
| 2012/0064622 A1 | 3/2012 | Fischer et al. | |
| 2015/0050708 A1 | 2/2015 | Burgard et al. | |
| 2015/0218528 A1 | 8/2015 | Bar-Even et al. | |

FOREIGN PATENT DOCUMENTS

WO  WO 2014/020599  2/2014

OTHER PUBLICATIONS

Advisory Action Before the Filing of an Appeal Brief dated Aug. 30, 2017 From the US Patent and Trademark Office Re. U.S. Appl. No. 14/417,559. (2 pages).
Communication Pursuant to Article 94(3) EPC dated Feb. 7, 2017 From the European Patent Office Re. Application No. 13759023.8. (5 Pages).
International Preliminary Report on Patentability dated Feb. 12, 2015 From the International Bureau of WIPO Re. Application No. PCT/IL2013/050643.
International Search Report and the Written Opinion dated Dec. 10, 2013 From the International Searching Authority Re. Application No. PCT/IL2013/050643.
Official Action dated May 1, 2017 From the US Patent and Trademark Office Re. U.S. Appl. No. 14/417,559. (8 pages).
Official Action dated Oct. 2, 2017 From the US Patent and Trademark Office Re. U.S. Appl. No. 14/417,559. (6 pages).
Official Action dated Oct. 14, 2016 From the US Patent and Trademark Office Re. U.S. Appl. No. 14/417,559.
Official Action dated Apr. 26, 2018 From the US Patent and Trademark Office Re. U.S. Appl. No. 14/417,559. (9 pages).
Restriction Official Action dated Jun. 16, 2016 From the US Patent and Trademark Office Re. U.S. Appl. No. 14/417,559.
Akhtar et al. "Construction of a Synthetic YdbK-Dependent Pyruvate:H2 Pathway in Escherichia coli BL21(DE3)", Metabolic Engineering 11: 139-147, 2009.
Bar-Even et al. "Design and Analysis of Metabolic Pathways Supporting Formatotrophic Growth for Electricity-Dependent Cultivatiob of Microbes", Biochimica et Biophysica Acta, XP055090015, 1827(8-9): 1039-1047, Oct. 30, 2012.
Bar-Even et al. "Design and Analysis of Synthetic Carbon Fixation Pathways", Proc. Natl. Acad. Sci. USA, PNAS, XP002638327, 107(19): 8889-8894, May 11, 2010.
Braakman et al. "Text S1: Supporting Methods", PLoS Computational Biology, XP055090478, P.1-6, Apr. 2012. Table S1.
Braakman et al. "The Emergence and Early Evolution of Biological Carbon- Fixation", PLoS Computational Biology, XP055090400, 8(4): e1002455-1-e1002455-16, Apr. 2012. P.5, col. 2, Last Para— P.6, col. 2, Fig.2, Table 1.
Friedrich et al. "Formate and Oxalate Metabolism in Alcaligenes Eutrophus", Journal of General Microbiology, 115: 185-192, 1979.

(Continued)

*Primary Examiner* — Maryam Monshipouri

(57) ABSTRACT

An isolated microorganism that expresses enzymes of the reductive glycine pathway is disclosed. The microorganism is capable of converting formate to pyruvate or glycerate via the formation of glycine and serine. Methods of generating same are further described.

19 Claims, 3 Drawing Sheets

Specification includes a Sequence Listing.

(56) References Cited

OTHER PUBLICATIONS

Fuchs "CO2 Fixation in Acetogenic Bacteria: Variations on a Theme (Acetogenic Bacteria, Methanogenic Bacteria, Sulfate-Reducing Bacteria, Carbon Monoxide Dehydrogenase, Autotrophy, Cobamides)", FEMS Microbiology Reviews, 39: 181-213, 1986.
Hawkins et al. "Extremely Thermophilic Routes to Microbial Electrofuels", ACM Catalysis, Biocatalysis and Biomemetic Catalysis for Sustainability, 1: 1043-1050, Aug. 1, 2011.
Lanthier et al. "Growth With High Planktonic Biomass in Shewanella Oneidensis Fuel Cells", FEMS Microbiology Letters, 278: 29-35, 2008.
Li et al. "Integrated Electromicrobial Conversion of CO2 to Higher Alcohols", Science, XP055090136, 335(6076): 1596, Mar. 30, 2012. Fig.1A.
Liu et al. "Microbial Electrolysis: Novel Biotechnology for Hydrogen Production From Biomass", Microbial Technology in Advanced Biofuels Production, Chap.6: 93-105, 2012.
Lovley "Powering Microbes With Electricity: Direct Electron Transfer From Electrodes to Microbes", Environmental Microbiology Reports, 3(1): 27-35, 2011.
Lovley et al. "A Shift in the Current: New Applications and Concepts for Microbe—Electrode Electron Exchange", Current Opinion in Biotechnology, 22: 441-448, Feb. 16, 2011.
Lovley et al. "Electricity Production With Electricigens", Bioenergy, Chap.23: 295-306, 2008.
Nevin et al. "Electrosynthesis of Organic Compounds From Carbon Dioxide Is Catalyzed by a Diversity of Acetogenic Microorganisms", Applied and Environmental Microbiology, 77(9): 28882-28886. Mar. 4, 2011.
Nevin et al. "Microbial Electrosynthesis: Feeding Microbes Electricity to Convert Carbon Dioxide and Water to Multicarbon Extracellular Organic Compounds", mBio, 1(2): e00103-10-1-e00103-10-4, May-Jun. 2010.
Ohmura et al. "Electrochemical Regeneration of Fe(III) to Support Growth on Anaerobic Iron Respiration", Applied and Environmental Microbiology, 68(1): 405-407, Jan. 2002.
Rabaey et al. "Metabolic and Practical Considerations on Microbial Electrosynthesis", Current Opinion in Biotechnology, 22: 371-377, Feb. 23, 2011.
Rabaey et al. "Microbial Electrosynthesis—Revisiting the Electrical Route for Microbial Production", Nature Reviews Microbiology, 8: 706-716, Oct. 2010.
Schneeberger et al. "Net Synthesis of Acetate From CO2 by Eubacterium Acidaminophilum Through the Glycine Reductase Pathway", FEMS Microbiology Letters, 177: 1-6, 1999.
Thrash et al. "Review: Direct and Indirect Electrical Stimulation of Microbial Metabolism", Environmental Science & Technology, 42(11): 3921-3931, 2008.
Veit et al. "Constructing and Testing the Thermodynamic Limits of Synthetic NAD(P)H:H2 Pathways", Microbial Biotechnology, 1(5): 382-394, Sep. 2008.

* cited by examiner

USE OF THE REDUCTIVE GLYCINE PATHWAY FOR GENERATING FORMATOTROPHIC AND AUTOTROPHIC MICROORGANISMS

RELATED APPLICATIONS

This application is a continuation of U.S. patent application Ser. No. 14/417,559 filed on Jan. 27, 2015, which is a National Phase of PCT Patent Application No. PCT/IL2013/050643 having International filing date of Jul. 29, 2013, which claims the benefit of priority under 35 USC § 119(e) of U.S. Provisional Patent Application No. 61/676,962 filed on Jul. 29, 2012. The contents of the above applications are all incorporated by reference as if fully set forth herein in their entirety.

SEQUENCE LISTING STATEMENT

The ASCII file, entitled 75510SequenceListing.txt, created on Oct. 17, 2018, comprising 60,221 bytes, submitted concurrently with the filing of this application is incorporated herein by reference.

FIELD AND BACKGROUND OF THE INVENTION

The present invention, in some embodiments thereof, relates to the use of the reductive glycine pathway for the generation of formatotrophic and autotrophic microorganisms.

The concept of biorefineries has become a wide spread notion in the last decade. It relies on the premise that living organisms can and should be used to supply the increasing demand by humanity for specialized chemicals, including fuels, solvents, plastics, pharmaceuticals, etc. Today, most of these chemicals are derived, directly or indirectly, from fissile carbons. However, with the imminent depletion of these fossil carbons and the increase in atmospheric $CO_2$ it has become essential to find alternative sources for these important materials.

The suggested feedstocks for most of the proposed biorefineries are simple sugars, starch, or lingocellulosic biomass. While the latter alternative has an apparent advantage over the former by not-competing with human consumption needs, it still presents numerous difficulties, including a problematic fermentation technology and feedstock availability and transportation. A fascinating alternative feedstock would be electric current. Electrons can be shuttled from an electrode to living cells, providing the necessary reducing equivalents and energy to support autotrophic growth and electrosynthesis of desired commodities (1-5). Since electricity is widely available, microbial electrosynthesis can be spatially and temporally decoupled from energy production and can take place at any convenient location and time.

Microbial electrosynthesis can be especially useful for the renewable energy market. One major drawback of most renewable energy sources, including solar, wind, hydro and nuclear, is that they are hard to store in a convenient way. Microbial electrosynthesis of fuels can thus serve to address this problem efficiently, converting electrical energy to kinetically stable chemical bonds.

Several methods of transferring reducing equivalents from an electrode to living cells were suggested and applied (reviewed in 1-5). Molecular hydrogen is one of the earliest electron carriers used in this manner since water electrolysis is a relatively mature technology that can support efficient hydrogen production at high current density. However, the use of hydrogen suffers from numerous problems including its low solubility and the risk of explosion. Moreover, the hydrogenase enzymes that transfer hydrogen's electrons to the cellular carriers are generally complex, oxygen sensitive proteins, which are hard to recombinantly express and consume a significant fraction of the cell resources. As an alternative to molecular hydrogen, several inorganic compounds, such as ferric ion or nitrate, can serve as electron shuttles, supporting electricity-dependent cultivation (5). However, since the reduction potentials of these compounds are considerably higher than that of NAD(P)H, reverse electron flow must take place during growth on these substrates, limiting electrosynthesis to specific organisms which are less suitable to industrial use. A further option is direct electron transfer from the cathode to the microbes. While several advantages of this option were proposed (reviewed in 2-5) this approach is limited to a small group of organisms or requires complex adaption of others.

As an alternative to all of the above methods, $CO_2$ can be directly reduced at the cathode (the electrons are derived from water splitting at the anode) (6), providing organic compounds that can be used by living cells as a source of reducing equivalents, energy and even carbon. A diverse group of compounds can be produced in this manner (6-9). The production of simple alcohols, such as methanol, ethanol and propanol, hydrocarbons, such as methane and ethylene, or acids with more than one carbon, such as acetic acid and oxalic acid, has the advantage of supplying microbes with compounds relatively simple to metabolize and/or being rich in reducing equivalents. However, the electrocatalytic production of all of these compounds is generally inefficient (not specific to a single product and/or requiring high overpotential), requiring costly catalysts and/or supporting low current density (reviewed in 6, 7). In contrast, there are two compounds that can be produced by direct reduction of $CO_2$ at relatively high efficiency (although lower than that of molecular hydrogen) and an acceptable current density: carbon monoxide and formic acid (6-13). Since carbon monoxide is a toxic and flammable gas with low solubility, formic acid, being readily soluble and of low toxicity, is a preferred mediator of electrons. In fact, a formate-based economy was recently proposed as an alternative to the hydrogen-based economy or methanol-based economy concepts (14-17).

Various methylotrophic organisms can grow on formate as a sole carbon, electron and energy source (18-21). Such organisms can be used for formate-dependent microbial electrosynthesis (19, 22). However, as compared to model organisms extensively used in the bioindustry, such as S. cerevisiae or E. coli, the metabolism of these microbes is far less understood, their bulk cultivation is limited and their genetic manipulation is considerably less optimized. As a consequence, biotechnological usage of these natural methylotrophs is usually limited to the production of simple products.

SUMMARY OF THE INVENTION

According to an aspect of some embodiments of the present invention there is provided an isolated microorganism that expresses enzymes of the reductive glycine pathway, wherein the microorganism is capable of converting formate to pyruvate or glycerate via the formation of glycine and serine.

According to an aspect of some embodiments of the present invention there is provided an isolated microorganism that expresses enzymes of the reductive glycine pathway, wherein the microorganism is capable of converting formate to a metabolite of central metabolism via the formation of glycine and without the formation of serine, the metabolite being selected from the group consisting of acetyl CoA, oxaloacetate and glycerate 2/3-phosphate.

According to an aspect of some embodiments of the present invention there is provided a method of generating a microorganism comprising expressing in the microorganism at least one enzyme of the reductive glycine pathway, such that the microorganism is capable of converting formate to pyruvate or glycerate via the formation of glycine and serine.

According to an aspect of some embodiments of the present invention there is provided a system for culturing the microorganism described herein and an electrode for providing electrons to generate formate.

According to an aspect of some embodiments of the present invention there is provided a method of selecting the microorganism described herein comprising:

growing a microorganism on formate; and analyzing for the production of metabolites of the reductive glycine pathway and/or activity of the enzymes of the reductive glycine pathway in the microorganism, wherein a production of the metabolites of the reductive glycine pathway and an activity of the enzymes of the reductive glycine pathway above a predetermined level is indicative of a formatotrophic microorganism.

According to an aspect of some embodiments of the present invention there is provided a method of generating a biofuel comprising culturing the microorganism described herein under conditions that allow for biofuel formation, thereby generating the biofuel.

According to an aspect of some embodiments of the present invention there is provided a method of generating a human polypeptide comprising culturing the microorganism described herein under conditions that allow for expression of the human polypeptide, thereby generating the human polypeptide.

According to some embodiments of the invention, the isolated microorganism is genetically modified.

According to some embodiments of the invention, the microorganism is genetically modified to express at least one of the enzymes of the reductive glycine pathway.

According to some embodiments of the invention, the microorganism is formatotrophic.

According to some embodiments of the invention, the microorganism further expresses a formate dehydrogenase which is capable of reducing carbon dioxide to formic acid.

According to some embodiments of the invention, the microorganism is autotrophic.

According to some embodiments of the invention, the microorganism is phototrophic.

According to some embodiments of the invention, the microorganism is chemotrophic.

According to some embodiments of the invention, the microorganism is aerobic.

According to some embodiments of the invention, the microorganism does not express EC 2.1.2.1.

According to some embodiments of the invention, the microorganism is anaerobic.

According to some embodiments of the invention, the microorganism is a bacteria.

According to some embodiments of the invention, the microorganism is a gram positive bacteria.

According to some embodiments of the invention, the microorganism is a gram negative bacteria.

According to some embodiments of the invention, the bacteria is selected from the group consisting of *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus,* and *Zymomonas.*

According to some embodiments of the invention, the bacteria comprises *Escherichia.*

According to some embodiments of the invention, the *Escherichia* are genetically modified to express a first enzyme NAD-dependent formate dehydrogenase which is capable of oxidizing formate to carbon dioxide and a second enzyme formate-tetrahydrofolate ligase.

According to some embodiments of the invention, the *Escherichia* are genetically modified to further express bifunctional methenyltetrahydrofolate-cyclohydrolase-NAD-dependent-methylenetetrahydrofolate-dehydrogenase.

According to some embodiments of the invention, the *Escherichia* are genetically modified to further express at least one glycine cleavage system enzyme.

According to some embodiments of the invention, the *Escherichia* are genetically modified to further express serine hydroxymethyltransferase and/or serine deaminase.

According to some embodiments of the invention, the microorganism is a yeast.

According to some embodiments of the invention, the yeast comprises *S. cervavisciae.*

According to some embodiments of the invention, the microorganism is a fungi.

According to some embodiments of the invention, the fungi is selected from *Aspergillus, Candida, Chlamydomonas, Chrysosporium, Cryotococcus, Fusarium, Kluyveromyces, Neotyphodium, Neurospora, Penicillium, Pichia, Saccharomyces, Trichoderma* and *Xanthophyllomyces.*

According to some embodiments of the invention, the microorganism is an algae.

According to some embodiments of the invention, the formatotrophic microorganism is genetically modified to express a human polypeptide.

According to some embodiments of the invention, the human polypeptide is selected from the group consisting of an antibody, insulin, interferon, growth hormone, erythropoietin, growth hormone, follicle stimulating hormone, factor VIII, low density lipoprotein receptor (LDLR) alpha galactosidase A and glucocerebrosidase.

According to some embodiments of the invention, the microorganism is capable of producing a biofuel.

According to some embodiments of the invention, the biofuel is selected from the group consisting of ethanol, propanol, isobutanol and n-butanol.

According to some embodiments of the invention, the biofuel is selected from the group consisting of an alcohol, an alkene, an alkane, a lipid or a polysaccharide.

According to some embodiments of the invention, the microorganism is formatotrophic.

According to some embodiments of the invention, the microorganism is autotrophic.

According to some embodiments of the invention, the method further comprises selecting the microorganism that is formatotrophic by growing the microorganism on formate following the expressing.

According to some embodiments of the invention, the method further comprises selecting the microorganism that is autotrophic by growing the microorganism on carbon dioxide in the presence of an external electron source following the expressing.

According to some embodiments of the invention, the method further comprises analyzing for the production of metabolites of the reductive glycine pathway and/or activity of the enzymes of the reductive glycine pathway in the microorganism.

According to some embodiments of the invention, the method further comprises culturing the microorganism following the generating.

According to some embodiments of the invention, the culturing is effected in a presence of an electrical current so as to generate the formate.

According to some embodiments of the invention, when the analyzing is for the production of metabolites, the method is effected by performing a pulse chase experiment.

According to some embodiments of the invention, the method further comprises analyzing for an expression of the enzymes of the reductive glycine pathway.

According to some embodiments of the invention, the method further comprises collecting the biofuel.

According to some embodiments of the invention, the method further comprises isolating the human polypeptide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to the use of the reductive glycine pathway for the generation of microorganisms and, more particularly, but not exclusively, to formatotrophic and autotrophic microorganisms.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Electrosynthesis has recently received much attention for being a promising approach for use of a renewable energy for the production of commodities by living cells. Several techniques were proposed to mediate the transfer of electrons from the cathode to living cells. Of these, the electroproduction of formate as a mediator seems to be especially interesting: formate is readily soluble, of low toxicity and can be produced at high efficiency and at reasonable current density.

There are numerous metabolic pathways that, once expressed in a microorganism, can potentially support formatotrophic growth. The present inventors applied diverse computational methods to analyze and compare these pathways according to various criteria including biomass yield, thermodynamic favorability, chemical motive force, kinetics and expression challenges and found that the reductive glycine pathway, composed of the tetrahydrofolate system, the glycine cleavage system, serine hydroxymethyltransferase and serine deaminase, displays superior characteristics and is the most promising candidate to mediate electrosynthesis using bacteria, and more specifically, E. coli as a host.

Figure 1:
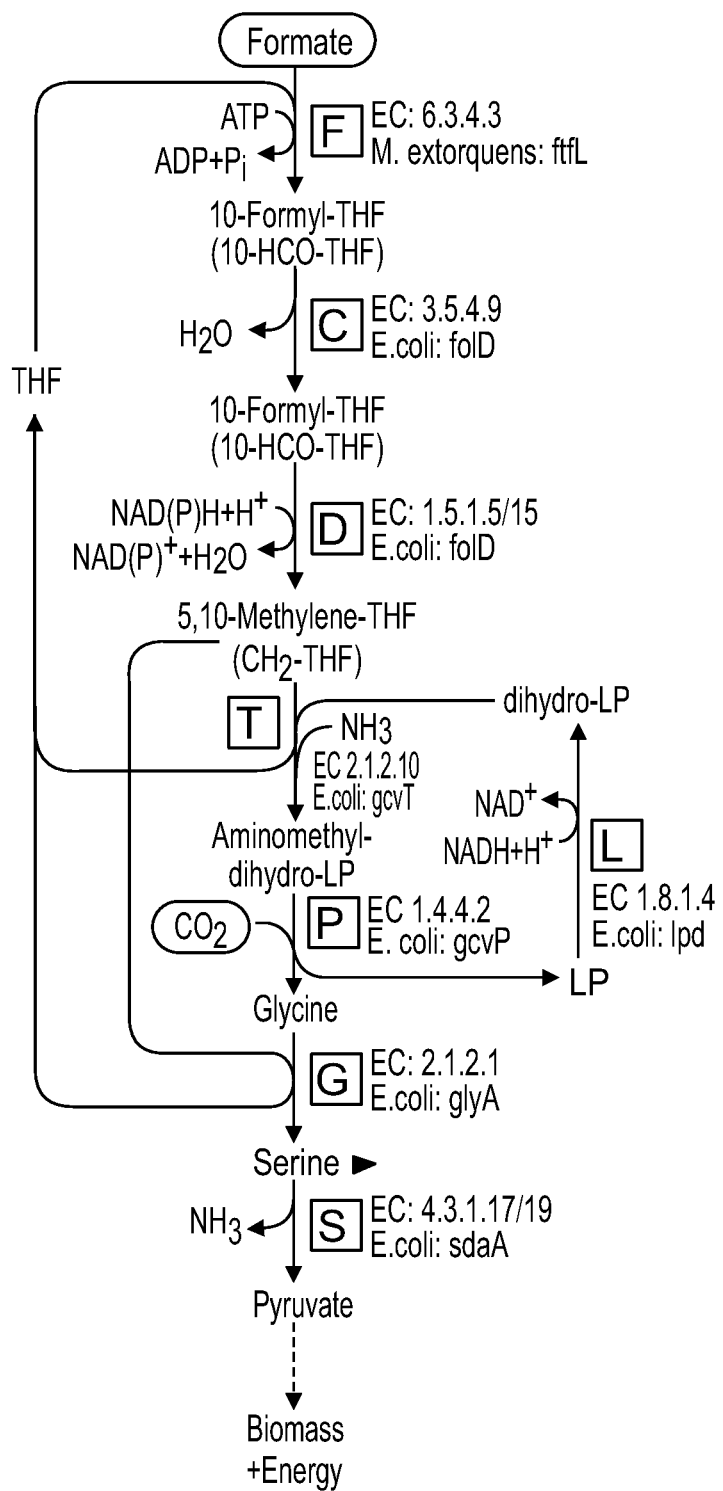
FIG. 1 is a diagram illustrating the reductive glycine pathway, producing pyruvate.

While organisms that are capable of formatotrophic growth, i.e. growth on formate, exist naturally, they are generally less suitable for metabolic engineering and bulk cultivation. Further, there is no indication that any organism uses this pathway to support methylotrophic or autotrophic growth. Microorganisms that do use the reductive glycine pathway as shown in FIG. 1, use it to generate an electron sink, recycling reduced electron carriers that are generated during the fermentation of purines and amino acids (23).

Thus, according to one aspect of the present invention there is provided an isolated microorganism that expresses enzymes of the reductive glycine pathway, wherein the microorganism is capable of converting formate to pyruvate or glycerate via the formation of glycine and serine.

As used herein, the term "microorganism" refers to any organism of microscopic size. Non-limiting examples of microorganisms as the term is used herein include both prokaryotic and eukaryotic microorganisms, such as bacteria, protozoan, fungi, molds, yeasts, algae etc. The microorganism may be aerobic or anaerobic.

The term "isolated" as used herein refers to a microorganism that is at least partially separated from the natural environment e.g., from other microorganisms that are not capable of using formate as a carbon, reducing power and energy source (e.g. purified or semi-purified). Contemplated populations of microorganisms are ones which are enriched for the microorganism described herein, e.g. wherein at least 30% thereof comprise the microorganism of the present invention, at least 40% thereof comprise the microorganism of the present invention, at least 50% thereof comprise the microorganism of the present invention, at least 60% thereof comprise the microorganism of the present invention, at least 70% thereof comprise the microorganism of the present invention, at least 80% thereof comprise the microorganism of the present invention, at least 90% thereof comprise the microorganism of the present invention, at least 95% thereof comprise the microorganism of the present invention.

The organisms can be fermentative organisms. Exemplary microorganisms include, for example, *Clostridium* (e.g., *C. acetobutylicum, C. Beijerinckii, C. saccharoperbutylacetonicum, C. saccharobutylicum, C. aurantibutyricum, C. tetanomorphum*), *Zymomonas, Escherichia* (e.g., *E. coli*), *Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula, Zymomonas* and *Saccharomyces*, e.g., *Saccharomyces cerevisiae, Saccharomyces carlsbergensis, Kluyveromyces lactis, Saccharomyces lactis*. Bacteria may be gram positive or gram negative. Examples of bacteria which are contemplated by the present invention include, but are not limited to *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*.

Examples of fungi contemplated by the present invention include, but are not limited to *Aspergillus, Candida, Chlamydomonas, Chrysosporium, Cryotococcus, Fusarium, Kluyveromyces, Neotyphodium, Neurospora, Penicillium* (e.g. *P. chrysogenum*), *Pichia, Saccharomyces, Trichoderma* and *Xanthophyllomyces*.

Examples of algae contemplated by the present invention include, but are not limited to a diatom or a cyanobacterium.

The diatom may be a microalgae of the class Coscinodiscophyceae, Fragilariophyceae or Bacillariophyceae.

The cyanobacterium can include, for example, *Botryococcus braunii, Chlorella, Dunaliella tertiolecta, Gracilaria, Pleurochrysis carterae, Sargassum* or *Ulva*.

The microorganism may be methylotrophic—i.e. is capable of growing on organic C1 compounds as their sole carbon, reducing power and energy source.

According to a particular embodiment, the methylotrophic microorganism is formatotrophic—i.e. uses formate as a carbon, reducing power and energy source. It will be appreciated that the formatotrophic organisms of the present invention may also be capable of growing on additional carbon sources—such as glucose, glycerol cellulose, acetate, butyrate, lactate, propionate, or valerate.

According to a particular embodiment, the formatotrophic uses formate as its sole carbon source.

According to another embodiment, the microorganism is autotrophic. One type of autotrophic microorganism is a phototrophic organism (one which requires light to get the reducing power and energy for carbon dioxide fixation). The electron source for photosynthesis may be for example, water, hydrogen sulfide, elemental sulfur or ferrous ion ($Fe^{2+}$).

Another type of autotrophic microorganism is a chemotrophic microorganism (one which requires an external electron source [e.g. molecular hydrogen, carbon monoxide (CO), hydrogen sulfide ($H_2S$), elemental sulfur (S), sulfite ($SO_3^{2-}$), phosphite ($PO_3^{2-}$), ammonia ($NH_4^+$), nitrite ($NO_2^{2-}$), ammonium hydroxide ($NH_2OH$), ferrous ion ($Fe^{2+}$), $Mn^{2+}$ ion] to get the reducing power and energy for carbon dioxide fixation). Possible terminal electron acceptors include molecular oxygen, carbon dioxide ($CO_2$), sulfate ($SO_4^{2-}$), elemental sulfur (S), nitrate ($NO_3^{2-}$), ferric ion ($Fe^{3+}$).

Figure 2:
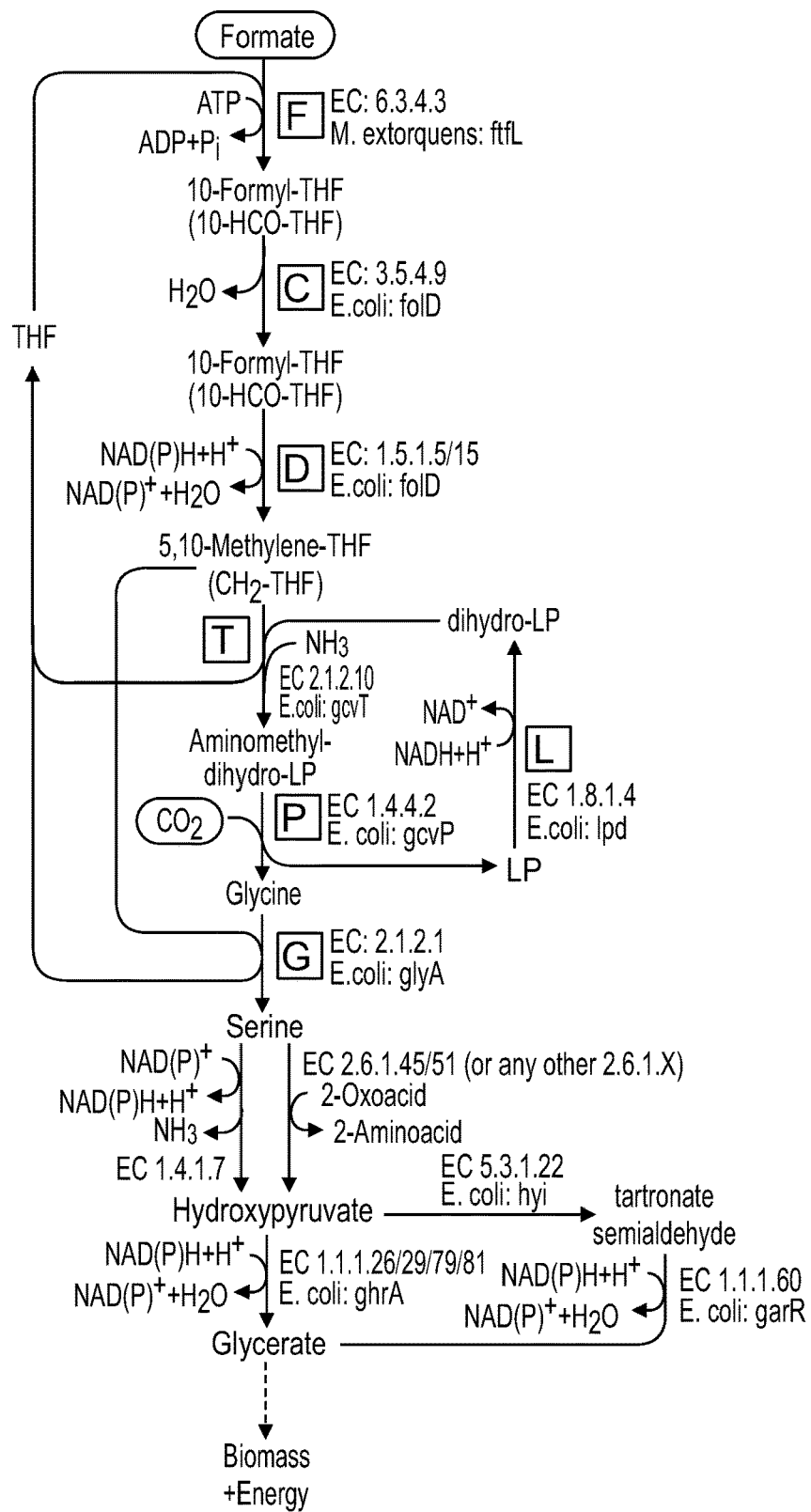
FIG. 2 is a diagram illustrating the reductive glycine pathway, producing glycerate.
Figure 3:
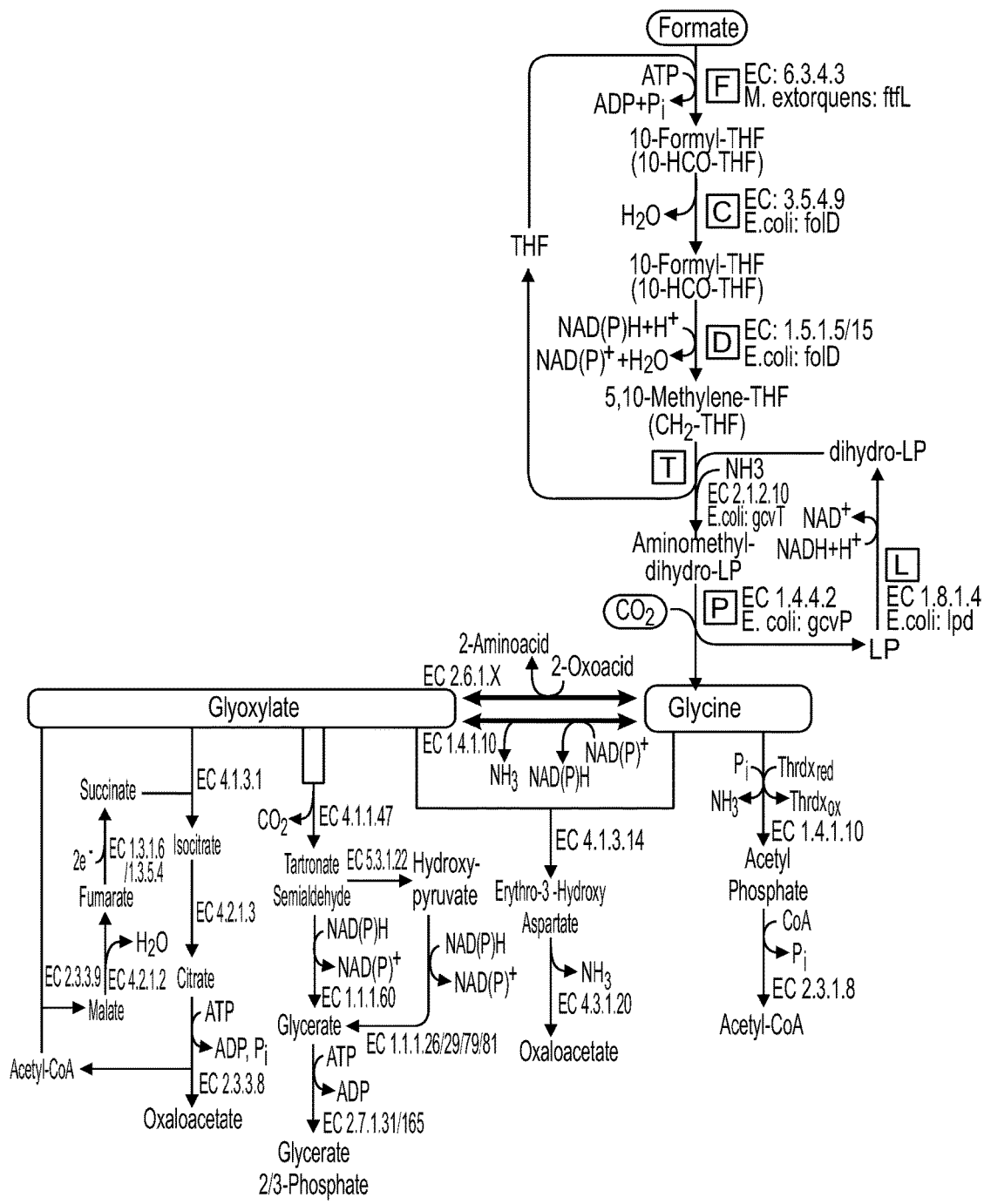
FIG. 3 is a diagram illustrating the reductive glycine pathway, in which glycine—and not serine—is assimilated into central metabolism

As mentioned the microorganisms of the present invention express, either naturally or are genetically engineered so as to express, enzymes of the reductive glycine pathway such that the microorganism is capable of converting formate to pyruvate via the formation of glycine and serine (FIG. 1) or is capable of converting formate to glycerate via the formation of glycine and serine (FIG. 2). A further alternative is using the enzymes of the reductive glycine pathway such that the microorganism is capable of converting formate to acetyl-CoA, glycerate or oxaloacetate via the formation of glycine, but without the formation of serine (FIG. 3).

The microorganism of embodiments of the present invention may use the enzyme serine deaminase for the conversion of the serine (generated via the reductive glycine pathway, FIG. 1) to pyruvate. Alternatively, the microorganism of embodiments of the present invention may use a serine transaminase enzyme (or serine dehydrogenase) and hydroxypyruvate reductase (or hydroxypyruvate isomerase and tartronate semialdehyde reductase) for the conversion of the serine (generated via the reductive glycine pathway) to glycerate (FIG. 2). Alternatively, the microorganism of embodiments of the present invention may directly assimilate glycine into central metabolism without producing serine, as shown in FIG. 3.

FIG. 1 illustrates the enzymes of the reductive glycine pathway in which the product is pyruvate. The pathway is composed of the tetrahydrofolate system, the glycine cleavage system, serine hydroxymethyltransferase and serine deaminase.

Thus, the microorganisms of the present invention may express formate tetrahydrofolate ligase (EC 6.3.4.3, THFS); methenyltetrahydrofolate cyclohydrolase (EC 3.5.4.9, folD); methylenetetrahydrofolate dehydrogenase (EC 1.5.1.5/15, folD); aminomethyltransferase (EC 2.1.2.10, gcvT); dihydrolipoyl dehydrogenase (EC1.8.1.4, lpd); glycine dehydrogenase (decarboxylating; EC 1.4.4.2, gcvP); serine hydroxymethyltransferase (EC2.1.2.1, glyA); and L-serine deaminase (EC 4.3.1.17, sdaA).

According to a particular embodiment the microorganism is capable of converting formate to pyruvate via an activity of serine deaminase or the microorganism is capable of converting formate to glycerate via an activity of a serine deaminase enzyme (e.g. EC 2.6.1.45, 2.6.1.51) and hydroxypyruvate reductase (EC 1.1.1.82 or 1.1.1.29).

The methenyltetrahydrofolate cyclohydrolase and methylenetetrahydrofolate dehydrogenase enzymes can be replaced by a bifunctional enzyme methenyltetrahydrofolate cyclohydrolase/methylenetetrahydrofolate dehydrogenase. Further, the enzyme formate tetrahydrofolate ligase and the bifunctional enzyme methenyltetrahydrofolate cyclohydrolase/methylenetetrahydrofolate dehydrogenase can be replaced by a trifunctional enzyme that carry formyl-THF synthethase, methenyltetrahydrofolate cyclohydrolase and methylenetetrahydrofolate dehydrogenase activities.

It will be appreciated that the enzyme formate tetrahydrofolate ligase can be bypassed by operating enzymes whose net reaction is identical to that of formate tetrahydrofolate ligase (for example, the sequential operation of purT (formate-dependent glycinamide ribonucleotide transformylase) in the forward direction and PurN (formyl-THF-dependent glycinamide ribonucleotide transformylase) in the reverse direction; another example is the sequential operation of purP (formate-dependent aminoimidazole carboxamide ribonucleotide transformylase) in the forward direction and PurH (formyl-THF-dependent aminoimidazole carboxamide ribonucleotide transformylase) in the reverse direction).

According to a particular embodiment the H-protein of the glycine cleavage system may also be expressed. In addition, the enzymes converting octanoic acid to lipoic acid attached to the H-protein (e.g. LipA, LipB and/or Lp1A) may also be expressed.

It will be appreciated that for the generation of formatotrophic microorganisms, expression of a formate deyhydrogenase (EC 1.2.1.2 or 1.2.1.43; for example GenBank CAB54834.1—SEQ ID NO: 12) which is capable of oxidizing formate to obtain carbon dioxide is also necessary. The electrons which are released serve as the reducing power required for the operation of the reductive glycine pathway and in order to generate ATP (e.g. via oxidative phosphorylation).

For the generation of autotrophic microorganisms, expression of a formate dehydrogenase which is capable of reducing carbon dioxide to formic acid is also necessary (EC 1.2.1.2, 1.2.1.43 or 1.1.99.33; for example GenBank AAB18330.2 (SEQ ID NO: 13) and AAB18329.1 (SEQ ID NO: 14).

Additional enzymes may also be expressed in the autotrophic microorganisms depending on the external electron source. Thus, for example if the electron source is hydrogen, the present invention contemplates expression of a hydrogenase enzyme. Further details on expression of hydrogenase in *E. coli* cells can be found in [24, 25].

FIG. 2 illustrates the enzymes of the reductive glycine pathway in which the product is glycerate.

Thus, the microorganisms of this aspect of the present invention may express formate tetrahydrofolate ligase (EC 6.3.4.3, THFS); methenyltetrahydrofolate cyclohydrolase (EC 3.5.4.9, folD); methylenetetrahydrofolate dehydrogenase (EC 1.5.1.5/15, folD); aminomethyltransferase (EC 2.1.2.10, gcvT); dihydrolipoyl dehydrogenase (EC 1.8.1.4, lpd); serine hydroxymethyltransferase (EC2.1.2.1, glyA); serine dehydrogenase (EC2.6.1.45) or serine-glyoxylate transaminase (EC 2.6.1.51) or any other transaminase enzyme (EC 2.6.1X); and hydroxypyruvate reductase (EC 1.1.1.26/19/79/81) or hydroxypyruvate isomerase (EC 5.3.1.22)+tartronate semialdehyde reductase (EC 1.1.1.60).

FIG. 3 illustrates the enzymes of the reductive glycine pathway in which the products are metabolites of central metabolism. In these microorganisms, the enzyme serine hydroxymethyltransferase (EC2.1.2.1, glyA) is not expressed.

Thus, the microorganisms of this aspect of the present invention may express formate tetrahydrofolate ligase (EC 6.3.4.3, THFS); methenyltetrahydrofolate cyclohydrolase (EC 3.5.4.9, folD); methylenetetrahydrofolate dehydrogenase (EC 1.5.1.5/15, folD); aminomethyltransferase (EC 2.1.2.10, gcvT); dihydrolipoyl dehydrogenase (EC1.8.1.4, lpd). When acetyl-CoA is produced as the central metabolite, the microorganism expresses the enzyme glycine reductase (EC 1.4.1.10) and phosphate acetyltransferase EC 2.3.1.8. Alternatively, glycine may be converted to glyoxylate and before being assimilated into central metabolism (as shown in FIG. 3). This requires the expression of glycine dehydrogenase (EC 1.4.1.10) or a transaminase (EC 2.6.1.51). When oxaloacetate is produced as the metabolite, the microorganism expresses enzymes EC 4.1.3.14 and 4.3.1.20. Alternatively, glycine may be converted to oxaloacetate via the reductive TCA cycle and glyoxylate shunt (as shown in FIG. 3). When glycerate 2-phosphate or glycerate 3-phosphate are produced, enzymes EC4.1.1.47, EC1.1.1.60 and EC 2.7.1.31/165 are expressed. As shown in FIG. 3, instead of EC1.1.1.60, the enzymes EC 5.3.1.22 and EC 1.1.1.26/29/79/81 may be expressed.

The term "enzyme" as used herein refers to a "catalytically functional biomolecule," which includes both whole native (or native-size) molecules and derivatives (e.g. genetic modifications) thereof.

Thus an enzyme of the present invention also refers to homologs and other modifications including additions or deletions of specific amino acids to the sequence (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to the lysomal amino acid sequences listed in Table 1, herein below as determined using BlastP software of the National Center of Biotechnology Information (NCBI) using default parameters). The homolog may also refer to an ortholog, a deletion, insertion, or substitution variant, including an amino acid substitution, thereof and biologically active polypeptide fragments thereof.

TABLE 1

| Enzyme | Examples of protein GenBank accession |
| --- | --- |
| formate tetrahydrofolate ligase (EC 6.3.4.3); | ABY28836.1 - SEQ ID NO: 1 |
| Bifunctional methenyltetrahydrofolate cyclohydrolase/ methylenetetrahydrofolate dehydrogenase (EC 3.5.4.9 and EC 1.5.1.5/15, folD) | NP_006627.2 - SEQ ID NO: 2 |
| aminomethyltransferase (EC 2.1.2.10, gcvT); and. | AAN81933.1 - SEQ ID NO: 3 |
| dihydrolipoyl dehydrogenase (EC 1.8.1.4, lpd) | ZP_03035757.1 - SEQ ID NO: 4 |
| glycine dehydrogenase (decarboxylating; EC 1.4.4.2, gcvP) | YP_005276541.1 - SEQ ID NO: 5 |
| serine hydroxymethyltransferase (EC 2.1.2.1, glyA) | ZP_03034169.1 - SEQ ID NO: 6 |
| L-serine deaminase; EC 4.3.1.17, sdaA) | AFH11608.1 - SEQ ID NO: 7 |
| serine -pyruvate transaminase (EC 2.6.1.51) | YP_004171157.1 - SEQ ID NO: 8 |
| hydroxypyruvate reductase (EC 1.1.1.81, ghrA) | ZP_04001524.1 - SEQ ID NO: 9 |
| serine-glyoxylate transaminase (EC 2.6.1.45) | YP_004370315.1 - SEQ ID NO: 10 |
| serine dehydrogenase (EC 1.4.1.7) | BAB07807.1 - SEQ ID NO: 11 |

Nucleic acid sequences encoding the enzymes of some embodiments of the invention may be optimized for expression for a particular microorganism. Examples of such sequence modifications include, but are not limited to, an altered G/C content to more closely approach that typically found in the microorganism species of interest, and the removal of codons atypically found in the microorganism species commonly referred to as codon optimization.

The phrase "codon optimization" refers to the selection of appropriate DNA nucleotides for use within a structural gene or fragment thereof that approaches codon usage within the microorganism of interest. Therefore, an optimized gene or nucleic acid sequence refers to a gene in which the nucleotide sequence of a native or naturally occurring gene has been modified in order to utilize statistically-preferred or statistically-favored codons within the microorganism. The nucleotide sequence typically is examined at the DNA level and the coding region optimized for expression in the microorganism species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed genes, followed by a calculation of the average squared deviation. The formula used is: 1 SDCU=n=1 N [(Xn−Yn)/Yn]2/N, where Xn refers to the frequency of usage of codon n in highly expressed genes, where Yn to the frequency of usage of codon n in the gene of interest and N refers to the total number of codons in the gene of interest.

One method of optimizing the nucleic acid sequence in accordance with the preferred codon usage for a particular cell type is based on the direct use, without performing any extra statistical calculations, of codon optimization tables such as those provided on-line at the Codon Usage Database through the NIAS (National Institute of Agrobiological Sciences) DNA bank in Japan (worldwidewebdotkazusa-dotordotjp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, E. coli), a naturally-occurring nucleotide sequence encoding a protein of interest can be codon optimized for that particular species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular species. Therefore, codon optimization of the native nucleotide sequence may comprise determining which codons, within the native nucleotide sequence, are not statistically-favored with regards to a particular plant, and modifying these codons in accordance with a codon usage table of the particular species to produce a codon optimized derivative. A modified nucleotide sequence may be fully or partially optimized for microorganism codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

To express the enzymes of the present invention using recombinant technology, polynucleotides encoding the enzymes may be ligated into a nucleic acid expression vector, under the transcriptional control of a cis-regulatory sequence (e.g., promoter sequence) suitable for directing constitutive or inducible transcription of the enzymes in the microorganism.

Thus, the present invention contemplates isolated polynucleotides encoding the enzymes of the present invention.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhancers) and transcription and translation terminators (e.g., polyadenylation signals).

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Exemplary bacterial based expression systems are disclosed in Baneyx et al., Current Opinion in Biotechnology, 1999; 10, 411-421 and Macrides et al, Microbiol Rev 1996, 60: 512-538, incorporated herein by reference.

The microorganisms may be transformed stably or transiently with the nucleic acid constructs of the present invention. In stable transformation, the nucleic acid molecule of the present invention is integrated into the microorganism genome and as such it represents a stable and inherited trait. In transient transformation, the nucleic acid molecule is expressed by the cell transformed but it is not integrated into the genome and as such it represents a transient trait.

The present invention contemplates using polynucleotide sequences which encode the enzymes of the reductive glycine pathway from any organism—e.g. human sequences, plant sequences, bacterial sequences, fungal sequences, yeast sequences.

It will be appreciated that the number of additional enzymes which have to be exogenously expressed in a particular microorganism will depend on the enzymes which are naturally expressed in that cell type and on the subcellular location thereof.

Thus, for example, in the case of *E. coli*, it is proposed that recombinant means are used to express:
1. NAD-dependent formate dehydrogenase which is capable of oxidizing formate to carbon dioxide; and
2. formate-tetrahydrofolate ligase.

In addition, expression of bifunctional methenyltetrahydrofolate-cyclohydrolase-NAD-dependent-methylenetetrahydrofolate-dehydrogenase may also be beneficial. Although endogenous to *E. coli*, overexpression of enzymes of the glycine cleavage system, serine hydroxymethyltransferase and serine deaminase are also contemplated.

Thus, for example, in the case of *S. cervavisciae*, it is proposed that recombinant means are used to express recombinant expression of NAD-dependent formate dehydrogenase, bifunctional methenyltetrahydrofolate-cyclohydrolase-NAD-dependent-methylenetetrahydrofolate-dehydrogenase and expression of an independent formate tetrahydrofolate ligase may also be beneficial. Enzymes of the glycine cleavage system should be expressed in the cytoplasm, since endogenously they are mitochondrial. Overexpression of cytoplasmatic serine hydroxymethyltransferase and serine deaminase is further contemplated.

Thus, for example, in the case of *B. subtilitis*, it is proposed that recombinant means are used to express formate-tetrahydrofolate ligase and serine deaminase. The recombinant expression of NAD dependent formate dehydrogenase and bifunctional methenyltetrahydrofolate-cyclohydrolase-NAD-dependent-methylenetetrahydrofolate-dehydrogenase may also be beneficial. Overexpression of enzymes of the glycine cleavage system and serine hydroxymethyltransferase is also contemplated.

Thus, for example, in the case of *Corynobacterium glutamicum*, it is proposed that recombinant means are used to express formate-tetrahydrofolate ligase, the glycine cleavage system enzymes (proteins H, P, T and H), and the enzymes converting octanoic acid to lipoic acid attached to the H-protein is required. The recombinant expression of NAD-dependent formate dehydrogenase and bifunctional methenyltetrahydrofolate-cyclohydrolase-NAD-dependent-methylenetetrahydrofolate-dehydrogenase may also be beneficial. Overexpression of serine hydroxymethyltransferase and serine deaminase is also contemplated.

Thus, for example, in the case of *Streptomyces* spp., recombinant expression of formate-tetrahydrofolate ligase is required. The recombinant expression of NAD-dependent formate dehydrogenase and bifunctional methenyltetrahydrofolate-cyclohydrolase-NAD-dependent-methylenetetrahydrofolate-dehydrogenase is further contemplated. Overexpression of enzymes of the glycine cleavage system, serine hydroxymethyltransferase and serine deaminase is also contemplated.

Thus, for example in the case of Lactococcus lactis, recombinant expression of the glycine cleavage system enzymes (proteins H, P, T and H), the enzymes converting octanoic acid to lipoic acid attached to the H-protein of the glycine cleavage system is required. The recombinant expression of NAD-dependent formate dehydrogenase and bifunctional methenyltetrahydrofolate-cyclohydrolase-NAD-dependent-methylenetetrahydrofolate-dehydrogenase is further contemplated. Over-expression of formate-tetrahydrofolate ligase, serine hydroxymethyltransferase and serine deaminase is also contemplated.

Transformed cells are cultured under effective conditions, which allow for the expression of high amounts of the recombinant enzymes. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

It will be appreciated that until the microorganism is transformed from being a heterotrophic microorganism to a formatotrophic microorganism or autotrophic microorganism, the microorganism is cultured in a culture medium comprising other carbon sources such as glucose or glycerol.

Following generation of the microorganisms as described herein, preferably they are selected by growing (i.e. culturing) on a particular substrate. Preferably, the microorganisms are grown for at least one day, at least two days, at least three days, at least one week, at least one month, at least three months wherein any viable cells remaining after such time are the selected microorganism.

Thus, for example in the case of generating a formatotrophic microorganism, the microorganism should be cultivated in a culture medium comprising formate as the carbon source. In the case of an autotrophic microorganism, the microorganism should be cultivated in a culture medium comprising carbon dioxide as the carbon source and an external electron source as further described herein above.

The formate which is used may come from any source—e.g. sodium formate, potassium formate, formic acid or formic acid anhydride etc.

Alternatively, and/or additionally, the formate may be generated using electricity. $CO_2$ can be directly reduced at the cathode (the electrons are derived from water splitting at the anode) to generate formate at relatively high efficiency.

In order to generate the formate for use by the microorganism, the microorganism is placed in a bioreactor in a fluid (e.g. water). The cathode may optionally be placed inside the bioreactor in contact with the microorganism. Alternatively, the cathode may be placed in a separate container to the bioreactor and the formate may be channeled to the chamber comprising the microorganism. The fluid may contain other elements required by the microorganism for growth including for example salts, minerals, metals and other nutrients, such as vitamins.

Examples of such bioreactors and further methods are provided in Li et al. Science, 2012, Vol 335, page 1596, Rabaey et al, Current Opinion in Biotechnology, 2011, 22: 371-377; Lovley et al., Current Opinion in Biotechnology, 2011, 22: 441-448; Lovley D. R., Environmental microbiology reports, 2011, 3(1), 27-35; Nevin et al., Microbiology, May/June 2010 Volume 1 Issue 2; Rabaey et al., Applied and Industrial Microbiology, Nature Reviews, October 2010, Volume 8, page 706-716; each of which are incorporated herein by reference.

The electrodes may be fabricated from such conductive polymers and metallic materials including indium tin oxide (ITO), graphite, platinum and silver.

Thus, a system is contemplated for the microorganism described herein and an electrode for providing electrons to generate formate. The system may further comprise mechanism(s) for separating, collecting, and/or recovering the biofuel which is generated by the microorganism (as further detailed below).

In order to confirm that the formatotrophic or autotrophic microorganism is using the reductive glycine pathway for generation of pyruvate or glycerate, the present invention further contemplates analysis of the metabolites of the reductive glycine pathway.

Such metabolites include 10-formyl-tetrahydrofolate, 5,10-methenyl-tetrahydrofolate, 5,10-methylene-tetrahydrofolate, aminomethyl-dihydrolipoylprotein, dihydrolypoylprotein, lypoylprotein, glycine, serine and pyruvate (or hydroxypyruvate and glycerate).

Preferably, the analysis comprises $^{13}$C- or $^{14}$C-labeling analysis for the time taken to produce each labeled metabolite from label formate, such that it is evident that production of 10-formyl-tetrahydrofolate precedes that of 5,10-methylene-tetrahydrofolate, such that the production of 5,10-methylene-tetrahydrofolate precedes that of aminomethyl-dihydrolipoyl, such that the production of aminomethyl-dihydrolipoyl precedes that of glycine, such that of production of glycine precedes that of serine and the production of serine precedes that of pyruvate.

Preferably, formation of each of the metabolites precedes the next one in the chain by at least one second, at least 10 seconds and more preferably at least 20 seconds.

An exemplary method for analyzing the timing of the production of metabolites is via pulse chase analysis. A pulse-chase analysis is a method for examining a cellular process occurring over time by successively exposing the cells to a labeled compound (pulse) and then to the same compound in an unlabeled form (chase). Radioactivity is a commonly used label.

In one exemplifying method, the microorganisms of embodiments of the invention are first exposed to labeled formate (the pulse). The labeled formate then goes through the metabolic pathways and is used in the synthesis of pyruvate. Shortly after introduction of the labeled formate (usually about 5 minutes), excess of the same, but unlabeled, formate (the chase) is introduced into the environment. The production of pyruvate would continue, but it would no longer contain the radioactive marker from the formate introduced in the pulse phase and would not be visible using radioactive detection methods.

In another exemplifying method, the compounds specified above can be analyzed to find which of their carbon atoms is labeled. If indeed they are produced via the reductive glycine pathway an indicative carbon-labeling pattern is expected.

The amount and/or activity of the enzymes of the pathway may be analyzed on the RNA or protein level using methods known in the art. Thus, on the RNA level, methods including RT-PCR, Northern blot analysis, oligonucleotide microarray. On the protein level, methods including ELISA, Western blot, radioimmunoassay, in situ activity assay, in vitro activity assay and immunohistochemical analysis are all contemplated. An indication for the pathway operation is if all pathway enzymes show activity sufficient to support cellular growth at the rate it has been shown to grow.

Further methods for analyzing production of metabolites of the reductive glycine pathway are found in Hugler et al, 2005, Methods In Enzymology, Vol. 397, p. 212-221; Berg et al., Science 318, 1782 (2007); Strauss et al., Eur. J. Biochem. 205, 853-866 (1992); Hertner et al., Journal Of Bacteriology, Vol 183, No. 14, July 2001, p. 4305-4316; Jahn et al., Journal Of Bacteriology, June 2007, p. 4108-4119 Vol. 189, No. 11; and Huber et al., PNAS Jun. 3, 2008, vol. 105, no. 22, 7851-7856, the contents of which are incorporated herein by reference.

According to one embodiment, the microorganism is one that produces an industrially important product—e.g. a biofuel. Alternatively, or additionally the microorganism expresses enzymes such that it is capable of producing an industrially important product—e.g. a biofuel. It will be appreciated that the precise choice of enzymes are selected according to the particular microorganism being used. Alternatively, or additionally the microorganism expresses an industrially important product—e.g. a recombinant protein. Additional industrial important products include antibiotics or other pharmaceutical, solvents, pigments, food additives, monomers for the plastic industry and industrially valuable polymers.

Biofuels include for example, an alcohol (e.g., methanol, ethanol, propanol, isobutanol, and n-butanol etc.), a hydrocarbon (e.g., an alkane such as methane, ethane, propane, butane, an alkene such as ethylene, propylene, isoprenes, an alkyne such as acetylene etc.) hydrogen, a biodiesel (long-chain alkyl (methyl, propyl or ethyl) esters), an aldehyde or ketones (e.g. acetone, formaldehyde, 1-propanal, etc.). The biofuel can be a solid, a liquid or a gas.

Industrially useful microorganisms include the production of ethanol by *Saccharomyces* and the production of butanol by *Clostridium*.

The recombinant protein may be any protein—e.g. a human protein used for medicinal purposes. Examples of such proteins include an antibody, insulin, interferon, growth hormone, erythropoietin, growth hormone, follicle stimulating hormone, factor VIII, low density lipoprotein receptor (LDLR) alpha galactosidase A and glucocerebrosidase.

As mentioned, in order to express recombinant proteins in the microorganism, polynucleotide sequences encoding same are inserted into expression vectors as described herein above.

It will be appreciated that other than containing the necessary elements for the transcription and translation of the inserted coding sequence (encoding the industrially useful polypeptide), the expression construct for expression of the industrially useful polypeptide can also include sequences engineered to optimize stability, production, purification, yield or activity of the expressed polypeptide.

Depending on the vector and host system used for production, resultant polypeptides of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site (e.g. 26, 27).

Recovery of biofuels may be recovered according to methods known in the art. Alcohols such as ethanol, methanol, and/or butanol may be recovered from liquid material by molecular sieves, distillation, and/or other separation techniques. For example, ethanol can be concentrated by fractional distillation to about 90% or about 95% by weight. There are several methods available to further purify ethanol beyond the limits of distillation, and these include drying (e.g., with calcium oxide or rocksalt), the addition of small quantities of benzene or cyclohexane, molecular sieve, membrane, or by pressure reduction.

Product gas, for example, as produced by anaerobic metabolism or photosynthesis, may be processed to separate the methane and/or hydrogen components. Methane, hydrogen, or biogas may be drawn off from the system as pipeline gas.

In accordance with the invention, methane and/or hydrogen may be recovered as a biofuel product. Methane may be recovered and/or purified from biogas by known methods and systems which are commercially available, including membrane systems known for separating gases on the basis of different permeabilities. See, for example, U.S. Pat. No. 6,601,543, which is hereby incorporated by reference. Alternatively, various methods of adsorption may be used for separating methane and hydrogen.

Other ways of collecting biofuel products including centrifugation, temperature fractionalization, chromatographic methods and electrophoretic methods.

In certain embodiments, the biofuel recovery/purification components may be integrated into the microorganism culturing system (e.g. bioreactor), for example, by connecting the respective device or apparatus to the gas or liquid effluents from the bioreactors. The purified biofuels and bioenergy products may be stoked in a separate container(s).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find calculated support in the following examples.

EXAMPLES

Reference is now made to the following examples, which together with the above descriptions illustrate some embodiments of the invention in a non limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Selecting an Optimum Pathway to Support Growth on Formate

To choose which of the pathways described above is most suitable to support growth on formate they were compared according to several criteria (28). First, the expected biomass yield on formate was calculated for each of the different pathway (21, 29, 30).

Two quantitative methods were used to estimate the biomass yield on formate of each of the pathways. In the "carbon-source-conversion" method (21), the present inventors first calculated the yield of converting formate into a designated benchmark metabolite, $Y_{formate \to metabolite}$, in units of mol/mol. Taking the experimentally measured biomass yield on that metabolite, $Y_{metabolite \to biomass}$, in units of gCDW/mol (CDW being cellular dry weight), one can then estimate the biomass yield on formate, in units of gCDW/mol formate, as $Y_{formate \to biomass} = Y_{formate \to metabolite} \cdot Y_{metabolite \to biomass}$.

For example, the present inventors calculated the number of formate molecules needed to be invested to generate one molecule of pyruvate. The reciprocal of this number is the pyruvate yield on formate in units of mol pyruvate/mol formate. Multiplying pyruvate yield on formate with biomass yield on pyruvate—14.7 gCDW/mol, as measured experimentally (31)—provided the inventors with an estimation for biomass yield on formate in units of gCDW/mol formate. The same process was then repeated for glucose, taking the experimentally measured biomass yield on glucose, 70.8 gCDW/mole (31). In both cases it was assumed that ATP is produced via NADH and oxidative phosphorylation and that the P/O ratio (measuring how many ATP molecules are produced per one oxygen atom being reduced) is 1.5, as is relevant for *E. coli* (32). The second and third column of Table 2 herein below displays the estimated biomass yield calculated by choosing either pyruvate or glucose as the product of the carbon fixation and formate-assimilating pathways.

uct gave much higher estimation for biomass yield on formate (~1.5 fold difference on average) just because the biomass yield of *E. coli* on glucose is higher than that on pyruvate.

An alternate approach to estimate biomass yield is to use flux balance analysis metrics (33, 34) as implemented by (30). The advantage of this approach is that it is not biased by the choice of metabolite to which formate is converted to and which is then used as a carbon source, but rather treat the entire cellular biomass as the product of carbon fixation or formate assimilation (30). The core *E. coli* metabolic model was selected (35) over the full metabolic model since the present inventors wanted to keep the analysis more general and less *E. coli* specific and since they wanted to avoid regulation complexities that can result in unsound solutions using the full metabolic model. Flux balance analysis was used to calculate growth yield rather than

TABLE 2

| | Biomass Yield, gCDW/mole-Formate * | | | | | |
|---|---|---|---|---|---|---|
| | Carbon-Source-Conversion | | Flux-Balance-Analysis | | | |
| | | | ATP | | | Number |
| Pathway | Formate conversion to pyruvate | Formate conversion to glucose | maintenance as for growth on glucose | With no ATP maintenance | Thermodynamics ** | of Foreign Enzymes *** |
| Carbon fixation pathways | | | | | | |
| reductive pentose phosphate | 1.5 | 3.0 | 2.5 | 5.6 | High CMF ‡ | 3 |
| reductive TCA | 2.3 | 3.8 | 2.9 | 6.7 | Unfavorable | 4 |
| dicarboxylate-4-hydroxypropionate | 1.8 | 3.1 | 2.4 | 5.3 | Low CMF | 5 |
| 3-hydroxypropionate-4-hydroxybutyrate | 1.3 | 2.5 | 1.8 | 4.2 | Low CMF | >5 |
| 3-hydroxypropionate | 1.5 | 2.8 | 1.9 | 4.4 | High CMF | >5 |
| MOG (28) | 1.6 | 3.1 | 2 | 4.5 | High CMF | >5 |
| Formate assimilating pathways | | | | | | |
| reductive acetyl-CoA | 2.6 | 4.1 | 2.7 | 6.2 | Unfavorable (High CMF) † | 4 |
| serine | 1.6 | 3.0 | 2.4 | 5.5 | High CMF | 5 |
| ribulose monophosphate | 2.1 | 3.8 | 2.8 | 6.4 | Low CMF | 4 |
| xylulose 5-phosphate | 1.9 | 3.5 | 2.6 | 5.9 | High CMF | 3 |
| Reductive glycine | 2.3 | 3.8 | 2.8 | 6.3 | High CMF (High CMF) †† | 2 |

\* see main text for the difference between the methods of calculating biomass yield on fromate.
\*\* Pathways marked with 'Unfavorable' contain a thermodynamically unfavorable reaction sequence; pathways marked with 'Low CMF' (i.e. low chemical motive force) are thermodynamically favorable but there is no metabolite concentration set, within the physiological range, that can support $\Delta G_r' < -3$ kJ/mol for all of its reactions; pathways marked with 'High CMF' are those for which such metabolite concentration set does exist.
\*\*\* Number of foreign enzymes that need to be expressed in *E. coli* to establish an active pathway.
‡ CMF stands for chemical motive force.
† The sign outside the parentheses refers to the case in which the reactions within the co-dehydrogenase-acetyl-coa-synthase complex are not coupled while the sign in the parentheses refers to the case they are coupled.
†† The sign outside the parentheses refers to the case in which the reactions within the glycine-cleavage-system complex are not coupled while the sign in the parentheses refers to the case they are coupled.

The results shown in Table 2 herein suggest that formate-assimilating pathways are generally more efficient than carbon fixation ones, with the exception of those carbon fixation pathways that bypass ATP-coupled carboxylation steps. Yet, these results also suggest that this type of analysis is problematic since the choice of the specific metabolite to serve as the product of the pathways can influence the estimation greatly: assuming glucose as the pathways' prodgrowth rate. Hence, formate input units were in mmol and biomass yield was given in gDW. Since the ATP maintenance cannot be estimated a priori for growth on formate the biomass yields were calculated in two different ways, once removing ATP maintenance altogether and once by assuming identical ATP maintenance to that of glucose. The fourth and fifth columns in Table 2 display the results of this analysis.

Importantly, while the methods of calculating biomass yield on formate differ substantially and resulted in up to 6 fold difference in estimated biomass yield (Table 2), they suggested very similar relative biomass yields of the pathways. In fact, the correlation between the biomass yields calculated by assuming pyruvate or glucose as the pathways' product and those calculated using flux balance analysis is $R^2 > 0.6$. Considering all the methods used, the reductive TCA cycle, reductive acetyl-coA pathway, ribulose monophosphate pathway and the reductive glycine pathway are the pathways supporting the highest biomass yield on formate.

Example 2

Thermodynamic Favorability

Not all metabolic pathways which operate in one organism are thermodynamically favorable in others, in which the cellular conditions (pH, ionic strength, etc.) might differ considerably (28, 36, 37). The present inventors therefore checked whether all the pathways discussed above are thermodynamically favorable within *E. coli* (pH~7.5, I~0.2 M). They tested not only the favorability of the pathway net reaction (28, 38) but also analyzed distributed thermodynamic bottlenecks composed of a subset of reactions within the pathways (28, 39). Notably, the CO-dehydrogenase-acetyl-CoA-synthase and the glycine-cleavage-system are complexes of several enzymes. Hence, the reactions that occur within these complexes are probably coupled to each other, overcoming any internal thermodynamic barrier (37). For pathways that contain these complexes both scenarios were considered—internal reactions within the complex are coupled or are uncoupled.

Two pathways were found that are predicted to be thermodynamically unfavorable since they contain reaction sets that cannot proceed in the forward direction at the cellular conditions of *E. coli* and under physiological reactant concentrations (the range 1 μM-10 mM for non co-factor metabolites was used) (37, 40-42). These are the reductive TCA cycle and the reductive acetyl-CoA pathway in which $CO_2$ reduction to CO and acetyl-CoA synthesis are not coupled. Both pathways are marked as 'unfavorable' in the sixth column of Table 2.

The sequential reductive operation of 2-ketoglutarate synthase and isocitrate dehydrogenase (part of the reductive TCA cycle), catalyzing the overall reaction succinyl-CoA+2 ferredoxin$^{red}$+NADPH+2 $CO_2$<=>isocitrate+CoA+2 ferredoxin$^{ox}$+NADP$^+$, seems to be unfavorable in *E. coli*. Even if it is assumed that the concentration of dissolved $CO_2$ is kept at 1 mM (~100 fold higher then ambient), [NADPH]=10-[NADP$^+$], [ferredoxin$^{red}$]~[ferredoxin$^{ox}$], [CoA]=1 mM (the lowest cellular concentration of this cofactor (40) and the other metabolites are at their possible extreme values, [succinyl–CoA]=10 mM and [isocitrate]=1 μM, the change in Gibbs energy ($\Delta_r G'$) during the overall reaction is still positive at pH 7.5 and I=0.2 M. This reasoning probably rules out the reductive TCA cycle from serving as a carbon fixation pathway in *E. coli*.

The energetic barrier of the reductive acetyl-CoA pathway is the result of the highly unfavorable reduction of $CO_2$ to CO with $\Delta_r G'^o = +46$ kJ/mol when ferredxoin serve as electron donor (43). However, this huge energetic barrier can be flattened altogether if the reaction is indeed coupled to the very favorable reaction that follows it within the same complex, acetyl-CoA synthase (37). In such a case the overall reaction, methyl-THF+$CO_2$+2 ferredoxin$^{red}$+CoA<=>acetyl-CoA+2 ferredoxin$^{ox}$+THF, will have $\Delta_r G'^o \sim -25$ kJ/mol (43), making the entire pathway favorable.

Example 3

Chemical Motive Force

Being thermodynamically favorable is not enough. The energy dissipated during a reaction ($\Delta_r G'$) can have a substantial effect on its kinetics. In fact, $\Delta G_r'$ dictates what fraction of the enzymatic machinery catalyzes the forward reaction (38, 44-46): $\Delta G_r' = -RT\ln(J^+/J^-)$, where $J^+$ is the forward flux, $J^-$ is the backward flux, R is the gas constant and T is the temperature in Kelvin. Hence, a low (negative) $\Delta G_r'$ value, corresponding to a high chemical motive force, indicates that most of the enzymatic machinery is catalyzing the forward reaction and hence a high metabolic rate can be achieved. Assuming substrate saturation and similar kinetics in the forward and backward direction, $\Delta G_r'$ of $-7.5$ kJ/mol corresponds to a reaction that proceeds at 90% of its maximal velocity: 95% of the enzymes catalyze the forward reaction while 5% catalyze the backward reaction.

The present inventors asked which of the pathways analyzed can, in principle, support high flux in terms of the chemical motive force sustained by each of its reactions. For each pathway a linear optimization tool was used to ask whether a metabolite concentration set exists, within the physiological range, such that each reaction of the pathway is not only favorable but also operate at $\Delta G_r' < -3$ kJ/mol, corresponding to at least 55% of its maximal rate (assuming substrate saturation and similar kinetics in the forward and backward direction). The sixth column in Table 2 displays the results. Pathways marked as 'low CMF' (low chemical motive force) are thermodynamically favorable but kinetically poorer since there is no metabolite concentration set, within the physiological range, that can support $\Delta G_r' < -3$ kJ/mol for all of its reactions. Pathways marked as 'high CMF' are those for which such metabolite concentration set does exist and hence, in potential, can sustain a high chemical motive force through the pathway.

Example 4

Pathway Kinetics

The chemical motive force is not the only parameter determining the reaction flux. The kinetic parameters, i.e. maximal velocity ($V_{MAX}$) and affinities toward the substrates (Michaelis constants, $K_M$), play a role no less important. The present inventors estimated what is the maximal growth rate for a bacterium utilizing formate only as an electron source and rely on carbon fixation pathways for carbon. They consider the growth rate limit imposed by the rate of formate dehydrogenase. Since formate dehydrogenase serves only auxiliary role in bacteria employing one of the formate-assimilating pathways (increasing cellular availability of reducing power and ATP), the analysis presented below do not hold in these cases.

Suppose that the cells express a formate dehydrogenase with a specific activity of 10 mol/min/mg (maximal velocity for the simple enzyme variants, see above) at 20% of its total protein (more than that is expected to be deleterious). Assuming that ~50% of the cellular dry weight is proteins (47), it is calculated that 10% of the cellular dry weight is formate dehydrogenase and hence the specific activity is ~1 μmol/min/mgCDW. If the reductive pentose phosphate pathway serves as the carbon fixation pathway, 12 NAD(P)H and 18 ATP molecules are required to fix six $CO_2$ molecules to glucose. Assuming a P/O ratio of 1.5 (32), 12+18/1.5=24 molecules of formate should be oxidized to support the formation of one glucose molecule. Hence, the rate of glucose formation will be $\frac{1}{24}$~0.042 mol-Glucose/min/mg CDW. Since the experimentally measured biomass yield on glucose is 70.8 gDW/mole (31) it is calculated that this rate to equal $0.042 \cdot 70.8 \cdot 10^{-6}$~$3 \cdot 10^{-6}$ gCDW/min/mgCDW or 0.003 mgCDW/min/mgCDW. Hence, the growth rate equals 0.0031/min and the doubling time is ln(2)/0.003~230 min~4 hours.

This calculation suggests that the doubling time of an autotrophic bacterium metabolizing formate using a formate dehydrogenase of the 'simple' type cannot be lower than 4 hours. Of course, this is only a lower limit and the doubling time might very well be limited by other factors, such as the rate of carbon fixation. In addition, even the rough limit of 4 hours can change when considering carbon fixation pathways with different ATP requirements or if restricting the expression of formate dehydrogenase to lower than 20% of total protein.

A similar kind of analysis can produce more conclusive results. For example, one can ask whether a bacterium can use the ribulose monophosphate or the xylulose 5-phosphate pathways for formate assimilation when limited by the rate of spontaneous cleavage of methylene-THF to formaldehyde and THF. According to the equilibrium and kinetic constants reported in (48) and assuming a high [methylene-THF]-10 mM, the maximal rate of methylene-THF cleavage can be calculated to be 0.027 mM/sec. Since the cellular volume of slowly growing $E.\ coli$ is ~1 $\mu m^3$ (49) this rate equals $2.7 \cdot 10^{-17}$ mmol/sec/cell or $1.6 \cdot 10^{-12}$ $\mu$mol/min/cell. Since six such reactions are required for the production of one glucose molecule the rate of glucose production is limited to $1.6 \cdot 10^{-12}/6 = 2.7 \cdot 10^{-13}$ $\mu$mol-Glucose/min/cell. The dry weight of an $E.\ coli$ cell with a volume of ~1 $\mu m^3$ is ~200 fg (50) and hence the former rate equals 0.0014 $\mu$mol-Glucose/min/mgCDW. According to the above biomass yield this rate corresponds to $9.6 \cdot 10^{-8}$ gCDW/min/mgCDW which is $9.6 \cdot 10^{-5}$ mgCDW/min/mgCDW. The growth rate therefore equals $9.6 \cdot 10^{-5}$ 1/min and the doubling time is $\ln(2)/(9.6 \cdot 10^{-5}) > 7200$ min=120 hours=5 days.

Therefore, this calculation suggests that, by considering only a single reaction, two formate-assimilating pathways are kinetically infeasible and cannot sustain even a minimally acceptable growth rate. Indeed, a previous study has demonstrated that the reverse reaction—the condensation of THF with formaldehyde—is too slow to have any metabolic significance in vivo (51).

Example 5

Pathway Expression Challenges

Finally, the present inventors asked how challenging the expression of an active pathway within $E.\ coli$ is expected to be. One aspect that affects the expression difficulty is the number of foreign enzymes that should be expressed to enable pathway activity. The seventh column in Table 2 displays this number for each of the metabolic alternatives. Notably, all pathways require, or are strongly benefiting from, the expression of formate dehydrogenase to supply the cell with reducing power and energy.

The reductive pentose phosphate pathway and the xylulose 5-phosphate pathway seem to impose a small expression barrier, necessitating only three foreign enzymes. The reductive glycine pathway presents the smallest expression barrier: only foreign formate dehydrogenase and formate-tetrahydrofolate ligase are needed for pathway operation.

The oxygen sensitivity of some of the enzymes operating in some of the pathways (38, 52) was also contemplated. Specifically, the reductive TCA cycle and the dicarboxylate-4-hydroxypropionate pathways employ several oxygen sensitive enzymes (38-52). Also, the reductive acetyl-CoA pathway operates some of the most oxygen sensitive enzymes known (38, 52, 53). These pathways are therefore not suitable if the bacterium is to be cultivated under aerobic conditions.

Concluding Remarks

Reviewing all the criteria suggests that one pathway stands out over the others. The reductive glycine pathway requires the expression of only two foreign enzymes, contains no oxygen sensitive enzyme, supports high biomass yield, is able to sustain high chemical motive force through the entire reaction set and is not severely kinetically restricted by any reaction (Table 1). This pathway seems to be the most promising route to establish a formatotrophic $E.\ coli$.

Some of the pathways analyzed by the present inventors have several variants, each with its own characteristics, advantages and drawbacks. For example, the reductive TCA cycle is probably not a good candidate since it contains a huge thermodynamic barrier at $E.\ coli$'s cellular conditions. However, $Hydrogenobacter\ thermophilus$ has evolved an ATP-dependent mechanism to push the pathway in the reductive direction: the enzyme 2-ketoglutarate carboxylase catalyzes the ATP-dependent carboxylation of 2-ketoglutarate to oxalosuccinate in a biotin-dependent mechanism, while oxalosuccinate is further reduced to isocitrate by a non-carboxylating isocitrate dehydrogenase (54, 55). This pathway variant is thermodynamically favorable and even supports high chemical motive force of each of its enzymatic components. However, the soluble intermediate oxalosuccinate is unstable and readily undergoes decarboxylation, hence creating a futile cycle that reduces the overall efficiency of carbon fixation (54).

Finally, enzyme evolution can provide numerous metabolic solutions to the challenges raised by the present inventors. For example, the enzyme catalyzing the reversible condensation of formaldehyde and tetrahydromethanopterin to methylene-tetrahydromethanopterin (56) can be evolved to accept THF instead of tetrahydromethanopterin, thereby lifting the kinetic barrier imposed by the spontaneous cleavage of methylene-THF. Of special importance is the design of an enzyme that can condense two formate molecules to glyoxylate which can then be directly assimilated into central metabolism. While such an enzyme was previously suggested to operate in the chloroplast of greening potato tubers (57-59), the energetics of this unactivated condensation is extremely unfavorable, indicating that the report is probably erroneous(38). Any attempt to design an enzyme that catalyzes this condensation must therefore first activate the formate (with a phosphate group, for example).

REFERENCES

[1] K. Rabaey, R. A. Rozendal, Microbial electrosynthesis—revisiting the electrical route for microbial production, Nat Rev Microbiol, 8 (2010) 706-716.

[2] D. R. Lovley, Powering microbes with electricity: direct electron transfer from electrodes to microbes, Env Microbilo Rep., 3 (2011) 27-35.

[3] D. R. Lovley, K. P. Nevin, A shift in the current: new applications and concepts for microbe-electrode electron exchange, Curr Opin Biotechnol, 22 (2011) 441-448.

[4] K. Rabaey, P. Girguis, L. K. Nielsen, Metabolic and practical considerations on microbial electrosynthesis, Curr Opin Biotechnol, 22 (2011) 371-377.

[5] J. C. Thrash, J. D. Coates, Review: Direct and Indirect Electrical Stimulation of Microbial Metabolism, Environ Sci Technol., 42 (2008) 3921-3931.

[6] D. T. Whipple, J. A. Kenis, Prospects of $CO_2$ Utilization via Direct Heterogeneous Electrochemical Reduction, J Phys Chem Lett., 1 (2010) 3451-3458.

[7] W. Li, Electrocatalytic Reduction of $CO_2$ to Small Organic Molecule Fuels on Metal Catalysts, in: Advances in $CO_2$ Conversion and Utilization, 2010, pp. 55-76.

[8] K. P. Kuhl, E. R. Cave, D. N. Abram, T. F. Jaramillo, New insights into the electrochemical reduction of carbon dioxide on metallic copper surfaces, Energy Environ Sci., 5 (2012) 7050-7059.

[9] E. A. Quadrelli, G. Centi, J. L. Duplan, S. Perathoner, Carbon dioxide recycling: emerging large-scale technologies with industrial potential, ChemSusChem, 4 (2011) 1194-1215.

[10] T. Reda, C. M. Plugge, N. J. Abram, J. Hirst, Reversible interconversion of carbon dioxide and formate by an electroactive enzyme, Proc Natl Acad Sci U.S.A., 105 (2008) 10654-10658.

[11] R. P. S. Chaplin, A. A. Wragg, Effects of process conditions and electrode material on reaction pathways for carbon dioxide electroreduction with particular reference to formate formation J Appl Electrochem., 33 (2003) 1107-1123.

[12] B. Innocent, D. Liaigre, D. Pasquier, F. Ropital, J.-M. Leger, K. B. Kokoh, Electro-reduction of carbon dioxide to formate on lead electrode in aqueous medium, J Appl Electrochem., 39 (2009) 227-232.

[13] C. Oloman, H. Li, Electrochemical processing of carbon dioxide, ChemSusChem, 1 (2008) 385-391.

[14] S. Enthaler, J. von-Langermann, T. Schmidt, Carbon dioxide and formic acid—the couple for environmental-friendly hydrogen storage?, Energy Environ Sci., 3 (2010) 1207-1217.

[15] J. H. Hull, Y. Himeda, W.-H. Wang, B. Hashiguchi, R. Periana, D. J. Szalda, J. T. Muckerman, E. Fujita, Reversible hydrogen storage using $CO_2$ and a proton-switchable iridium catalyst in aqueous media under mild temperatures and pressures, Nature Chemistry, 4 (2012) 383-388.

[16] F. Joo, Breakthroughs in hydrogen storage—formic Acid as a sustainable storage material for hydrogen, ChemSusChem, 1 (2008) 805-808.

[17] B. Loges, A. Boddien, F. Gartner, H. Junge, M. Beller, Catalytic Generation of Hydrogen from Formic acid and its Derivatives: Useful Hydrogen Storage Materials Top Catal, 53 (2010) 902-914.

[18] M. E. Lidstrom, Aerobic Methylotrophic Prokaryotes, in: M. Dworkin, S. Falkow, E. Rosenberg, K. H. Schleifer, E. Stackebrandt (Eds.) The Prokaryotes, Springer, New York, 2006, pp. 618-634.

[19] J. Schrader, M. Schilling, D. Holtmann, D. Sell, M. V. Filho, A. Marx, J. A. Vorholt, Methanol-based industrial biotechnology: current status and future perspectives of methylotrophic bacteria, Trends Biotechnol, 27 (2009) 107-115.

[20] L. Chistoserdova, M. G. Kalyuzhnaya, M. E. Lidstrom, The expanding world of methylotrophic metabolism, Annu Rev Microbiol, 63 (2009) 477-499.

[21] C. Anthony, The Biochemistry of Methylotrophs, Academic Press, London; New-York, 1982.

[22] H. Li, P. H. Opgenorth, D. G. Wernick, S. Rogers, T. Y. Wu, W. Higashide, P. Malati, Y. X. Huo, K. M. Cho, J. C. Liao, Integrated electromicrobial conversion of CO2 to higher alcohols, Science, 335 (2012) 1596.

[23] G. Fuchs, CO2 fixation in acetogenic bacteria: variations on a theme, FEMS Microbiology Letters, 39 (1985) 181-213.

[24] A. Veit, M. K. Akhtar, T. Mizutani, P. R. Jones, Constructing and testing the thermodynamic limits of synthetic NAD(P)H:H2 pathways, Microb Biotechnol, 1 (2008) 382-394.

[25] M. K. Akhtar, P. R. Jones, Construction of a synthetic YdbK-dependent pyruvate:H2 pathway in *Escherichia coli* BL21(DE3), Metab Eng, 11 (2009) 139-147.

[26] R. J. Booth, P. M. Grandison, R. L. Prestidge, J. D. Watson, The use of a 'universal' yeast expression vector to produce an antigenic protein of *Mycobacterium leprae*, Immunol Lett, 19 (1988) 65-69.

[27] T. J. Gardella, D. Rubin, A. B. Abou-Samra, H. T. Keutmann, J. T. Potts, Jr., H. M. Kronenberg, S. R. Nussbaum, Expression of human parathyroid hormone-(1-84) in *Escherichia coli* as a factor X-cleavable fusion protein, J Biol Chem, 265 (1990) 15854-15859.

[28] A. Bar-Even, E. Noor, N. E. Lewis, R. Milo, Design and analysis of synthetic carbon fixation pathways, Proc Natl Acad Sci U.S.A., 107 (2010) 8889-8894.

[29] I. Goldberg, J. S. Rock, A. Ben-Bassat, R. I. Mateles, Bacterial yields on methanol, methylamine, formaldehyde, and formate, Biotechnol Bioeng, 18 (1976) 1657-1668.

[30] N. R. Boyle, J. A. Morgan, Computation of metabolic fluxes and efficiencies for biological carbon dioxide fixation, Metab Eng, 13 (2011) 150-158.

[31] K. B. Andersen, K. von Meyenburg, Are growth rates of *Escherichia coli* in batch cultures limited by respiration?, J Bacteriol, 144 (1980) 114-123.

[32] Y. Noguchi, Y. Nakai, N. Shimba, H. Toyosaki, Y. Kawahara, S. Sugimoto, E. Suzuki, The energetic conversion competence of *Escherichia coli* during aerobic respiration studied by 31P NMR using a circulating fermentation system, J Biochem, 136 (2004) 509-515.

[33] J. D. Orth, I. Thiele, B. O. Palsson, What is flux balance analysis?, Nat Biotechnol, 28 (2010) 245-248.

[34] K. Raman, N. Chandra, Flux balance analysis of biological systems: applications and challenges, Brief Bioinform, 10 (2009) 435-449.

[35] J. D. Orth, R. M. T. Fleming, B. O. Palsson, The Core *E. coli* Model, in, gcrgdotucsddotedu/Downloads/ EcoliCore, 2009.

[36] R. A. Alberty, Thermodynamics of Biochemical Reactions, Wiley-Interscience, 2003.

[37] A. Bar-Even, A. Flamholz, E. Noor, R. Milo, Thermodynamic constraints shape the structure of carbon fixation pathways, Biochim Biophys Acta, (2012).

[38] A. Bar-Even, E. Noor, R. Milo, A survey of carbon fixation pathways through a quantitative lens, J Exp Bot, 63 (2012) 2325-2342.

[39] M. L. Mavrovouniotis, Identification of localized and distributed bottlenecks in metabolic pathways, Proc Int Conf Intell Syst Mol Biol, 1 (1993) 275-283.

[40] B. D. Bennett, E. H. Kimball, M. Gao, R. Osterhout, S. J. Van Dien, J. D. Rabinowitz, Absolute metabolite concentrations and implied enzyme active site occupancy in *Escherichia coli*, Nat Chem Biol, 5 (2009) 593-599.

[41] A. Bar-Even, E. Noor, A. Flamholz, J. M. Buescher, R. Milo, Hydrophobicity and charge shape cellular metabolite concentrations, PLoS Comput Biol, 7 (2011) e1002166.

[42] E. Noor, A. Bar-Even, A. Flamholz, Y. Lubling, D. Davidi, R. Milo, An integrated open framework for thermodynamics of reactions that combines accuracy and coverage, Bioinformatics, published online (2012).

[43] A. Flamholz, E. Noor, A. Bar-Even, R. Milo, eQuilibrator—the biochemical thermodynamics calculator, Nucleic Acids Res, 40 (2011) D700-D775.

[44] H. Qian, D. A. Beard, S. D. Liang, Stoichiometric network theory for nonequilibrium biochemical systems, Eur J Biochem, 270 (2003) 415-421.

[45] D. A. Beard, H. Qian, Relationship between thermodynamic driving force and one-way fluxes in reversible processes, PLoS One, 2 (2007) e144.

[46] A. Bar-Even, A. Flamholz, E. Noor, R. Milo, Rethinking glycolysis: on the biochemical logic of metabolic pathways, Nat Chem Biol, 8 (2012) 509-517.

[47] H. Bremer, P. Dennis, Modulation of chemical composition and other parameters of the cell by growth rate, in: *Escherichia coli* and *Salmonella*, 1987.

[48] R. G. Kallen, W. P. Jencks, The mechanism of the condensation of formaldehyde with tetrahydrofolic acid, J Biol Chem, 241 (1966) 5851-5863.

[49] B. Volkmer, M. Heinemann, Condition-dependent cell volume and concentration of *Escherichia coli* to facilitate data conversion for systems biology modeling, PLoS One, 6 (2011) e23126.

[50] M. Loferer-Krossbacher, J. Klima, R. Psenner, Determination of bacterial cell dry mass by transmission electron microscopy and densitometric image analysis, Appl Environ Microbiol, 64 (1998) 688-694.

[51] G. J. Crowther, G. Kosaly, M. E. Lidstrom, Formate as the main branch point for methylotrophic metabolism in Methylobacterium extorquens AM1, J Bacteriol, 190 (2008) 5057-5062.

[52] I. A. Berg, Ecological Aspects of the Distribution of Different Autotrophic CO2 Fixation Pathways, Appl Environ Microbiol, 77 (2011) 1925-1936.

[53] H. L. Drake, K. Kirsten, C. Matthies, Acetogenic Prokaryotes in: The Prokaryotes, Springer New York, 2006, pp. 354-420.

[54] M. Aoshima, Y. Igarashi, A novel oxalosuccinate-forming enzyme involved in the reductive carboxylation of 2-oxoglutarate in Hydrogenobacter thermophilus TK-6, Mol Microbiol, 62 (2006) 748-759.

[55] M. Aoshima, M. Ishii, Y. Igarashi, A novel biotin protein required for reductive carboxylation of 2-oxoglutarate by isocitrate dehydrogenase in Hydrogenobacter thermophilus TK-6, Mol Microbiol, 51 (2004) 791-798.

[56] J. A. Vorholt, C. J. Marx, M. E. Lidstrom, R. K. Thauer, Novel formaldehyde-activating enzyme in *Methylobacterium extorquens* AM1 required for growth on methanol, J Bacteriol, 182 (2000) 6645-6650.

[57] N. K. Ramaswamy, A. G. Behere, P. M. Nair, A novel pathway for the synthesis of solanidine in the isolated chloroplast from greening potatoes, Eur J Biochem, 67 (1976) 275-282.

[58] M. T. Janave, N. K. Ramaswamy, P. M. Nair, Purification and characterization of glyoxylate synthetase from greening potato-tuber chloroplasts, Eur J Biochem, 214 (1993) 889-896.

[59] M. T. Janave, N. K. Ramaswamy, P. M. Nair, Studies on determination of active site amino acid residues in glyoxylate synthetase from potato tuber chloroplasts, Plant Physiology and Biochemistry, 37 (1999) 121-129.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated microoranism that is genetically modified to overexpress at least one enzyme of the glycine cleavage system, said enzyme being selected from the group consisting of EC 2.1.2.10, EC1.8.1.4 and EC 1.4.4.2, wherein the microorganism is able to utilize formate as a carbon source for the generation of pyruvate or glycerate via the formation of glycine and serine.

2. An isolated microorganism that is genetically modified to express enzymes of the reductive glycine pathway, wherein the microorganism is capable of converting formate to a metabolite of central metabolism via the formation of glycine and without the formation of serine, said metabolite being selected from the group consisting of acetyl CoA, oxaloacetate, glycerate 2-phosphate and glycerate 3-phosphate, wherein said microorganism uses formate as its carbon source.

3. The microorganism of claim 2, not expressing EC 2.1.2.1.

4. The microorganism of claim 1, further expressing a formate dehydrogenase which is capable of reducing carbon dioxide to formic acid.

5. The microorganism of claim 1, selected from the group consisting of a fungus and an algae.

6. The microorganism of claim 2, selected from the group consisting of a bacteria, a fungus and an algae.

7. The microorganism of claim 1, being genetically modified to express a human polypeptide.

8. The microorganism of claim 1, capable of producing a biofuel.

9. A method of generating a microorganism comprising overexpressing in the microorganism at least one enzyme of the glycine cleavage system, said enzyme being selected from the group consisting of EC 2.1.2.10, EC1.8.1.4 and EC 1.4.4.2, wherein the microorganism is capable of utilizing formate as a carbon source for the generation of pyruvate or glycerate via the formation of glycine and serine.

10. The method of claim 9, wherein said microorganism is formatotrophic.

11. The method of claim 9, wherein said microorganism is autotrophic.

12. The method of claim 10, further comprising selecting the microorganism that is formatotrophic by growing the microorganism on formate following said expressing.

13. The method of claim 11, further comprising selecting the microorganism that is autotrophic by growing the microorganism on carbon dioxide in the presence of an external electron source following said expressing.

14. The method of claim 9, further comprising culturing said microorganism following said generating.

15. The method of claim 14, wherein said culturing is effected in a presence of an electrical current so as to generate said formate.

16. The microorganism of claim 1, further expressing a NAD-dependent formate dehydrogenase which is capable of oxidizing formate to carbon dioxide.

17. The microorganism of claim 2, further expressing a NAD-dependent formate dehydrogenase which is capable of oxidizing formate to carbon dioxide.

18. The microorganism of claim 5, wherein the fungus is a yeast.

19. The microorganism of claim 6, wherein the fungus is a yeast.

* * * * *

SEQUENCE LISTING

<160> NUMBER OF SEQ ID NOS: 14

<210> SEQ ID NO 1
<211> LENGTH: 557
<212> TYPE: PRT
<213> ORGANISM: Methylobacterium extorquens PA1

<400> SEQUENCE: 1

Met Pro Ser Asp Ile Glu Ile Ala Arg Ala Ala Thr Leu Lys Pro Ile
1               5                   10                  15

Ala Gln Val Ala Glu Lys Leu Gly Ile Pro Asp Glu Ala Leu His Asn
            20                  25                  30

Tyr Gly Lys His Ile Ala Lys Ile Asp His Asp Phe Ile Ala Ser Leu
        35                  40                  45

Glu Gly Lys Pro Glu Gly Lys Leu Val Leu Val Thr Ala Ile Ser Pro
    50                  55                  60

Thr Pro Ala Gly Glu Gly Lys Thr Thr Thr Val Gly Leu Gly Asp
65                  70                  75                  80

Ala Leu Asn Arg Ile Gly Lys Arg Ala Val Met Cys Leu Arg Glu Pro
                85                  90                  95

```
Ser Leu Gly Pro Cys Phe Gly Met Lys Gly Ala Ala Gly Gly Gly
            100                 105                 110

Lys Ala Gln Val Val Pro Met Glu Gln Ile Asn Leu His Phe Thr Gly
            115                 120                 125

Asp Phe His Ala Ile Thr Ser Ala His Ser Leu Ala Ala Ala Leu Ile
130                 135                 140

Asp Asn His Ile Tyr Trp Ala Asn Glu Leu Asn Ile Asp Val Arg Arg
145                 150                 155                 160

Ile His Trp Arg Arg Val Val Asp Met Asn Asp Arg Ala Leu Arg Ala
                165                 170                 175

Ile Asn Gln Ser Leu Gly Gly Val Ala Asn Gly Phe Pro Arg Glu Asp
            180                 185                 190

Gly Phe Asp Ile Thr Val Ala Ser Glu Val Met Ala Val Phe Cys Leu
            195                 200                 205

Ala Lys Asn Leu Ala Asp Leu Glu Glu Arg Leu Gly Arg Ile Val Ile
            210                 215                 220

Ala Glu Thr Arg Asp Arg Lys Pro Val Thr Leu Ala Asp Val Lys Ala
225                 230                 235                 240

Thr Gly Ala Met Thr Val Leu Leu Lys Asp Ala Leu Gln Pro Asn Leu
                245                 250                 255

Val Gln Thr Leu Glu Gly Asn Pro Ala Leu Ile His Gly Gly Pro Phe
            260                 265                 270

Ala Asn Ile Ala His Gly Cys Asn Ser Val Ile Ala Thr Arg Thr Gly
            275                 280                 285

Leu Arg Leu Ala Asp Tyr Thr Val Thr Glu Ala Gly Phe Gly Ala Asp
            290                 295                 300

Leu Gly Ala Glu Lys Phe Ile Asp Ile Lys Cys Arg Gln Thr Gly Leu
305                 310                 315                 320

Lys Pro Ser Ala Val Ile Val Ala Thr Ile Arg Ala Leu Lys Met
                325                 330                 335

His Gly Gly Val Asn Lys Lys Asp Leu Gln Ala Glu Asn Leu Asp Ala
                340                 345                 350

Leu Glu Lys Gly Phe Ala Asn Leu Glu Arg His Val Asn Asn Val Arg
            355                 360                 365

Ser Phe Gly Leu Pro Val Val Val Gly Val Asn His Phe Phe Gln Asp
370                 375                 380

Thr Asp Ala Glu His Ala Arg Leu Lys Glu Leu Cys Arg Asp Arg Leu
385                 390                 395                 400

Gln Val Glu Ala Ile Thr Cys Lys His Trp Ala Glu Gly Gly Ala Gly
                405                 410                 415

Ala Glu Ala Leu Ala Gln Ala Val Lys Leu Ala Glu Gly Glu Gln
            420                 425                 430

Lys Pro Leu Thr Phe Ala Tyr Glu Thr Glu Thr Lys Ile Thr Asp Lys
            435                 440                 445

Ile Lys Ala Ile Ala Thr Lys Leu Tyr Gly Ala Ala Asp Ile Gln Ile
            450                 455                 460

Glu Ser Lys Ala Ala Thr Lys Leu Ala Gly Phe Glu Lys Asp Gly Tyr
465                 470                 475                 480

Gly Lys Leu Pro Val Cys Met Ala Lys Thr Gln Tyr Ser Phe Ser Thr
                485                 490                 495

Asp Pro Thr Leu Met Gly Ala Pro Ser Gly His Leu Val Ser Val Arg
                500                 505                 510
```

-continued

Asp Val Arg Leu Ser Ala Gly Ala Gly Phe Val Val Ile Cys Gly
    515                 520                 525

Glu Ile Met Thr Met Pro Gly Leu Pro Lys Val Pro Ala Ala Asp Thr
530                 535                 540

Ile Arg Leu Asp Ala Asn Gly Gln Ile Asp Gly Leu Phe
545                 550                 555

<210> SEQ ID NO 2
<211> LENGTH: 350
<212> TYPE: PRT
<213> ORGANISM: Homo sapiens

<400> SEQUENCE: 2

Met Ala Ala Thr Ser Leu Met Ser Ala Leu Ala Ala Arg Leu Leu Gln
1               5                   10                  15

Pro Ala His Ser Cys Ser Leu Arg Leu Arg Pro Phe His Leu Ala Ala
            20                  25                  30

Val Arg Asn Glu Ala Val Val Ile Ser Gly Arg Lys Leu Ala Gln Gln
        35                  40                  45

Ile Lys Gln Glu Val Arg Gln Glu Val Glu Glu Trp Val Ala Ser Gly
    50                  55                  60

Asn Lys Arg Pro His Leu Ser Val Ile Leu Val Gly Glu Asn Pro Ala
65                  70                  75                  80

Ser His Ser Tyr Val Leu Asn Lys Thr Arg Ala Ala Val Val Gly
                85                  90                  95

Ile Asn Ser Glu Thr Ile Met Lys Pro Ala Ser Ile Ser Glu Glu Glu
            100                 105                 110

Leu Leu Asn Leu Ile Asn Lys Leu Asn Asn Asp Asn Val Asp Gly
        115                 120                 125

Leu Leu Val Gln Leu Pro Leu Pro Glu His Ile Asp Glu Arg Arg Ile
    130                 135                 140

Cys Asn Ala Val Ser Pro Asp Lys Asp Val Asp Gly Phe His Val Ile
145                 150                 155                 160

Asn Val Gly Arg Met Cys Leu Asp Gln Tyr Ser Met Leu Pro Ala Thr
                165                 170                 175

Pro Trp Gly Val Trp Glu Ile Ile Lys Arg Thr Gly Ile Pro Thr Leu
            180                 185                 190

Gly Lys Asn Val Val Ala Gly Arg Ser Lys Asn Val Gly Met Pro
        195                 200                 205

Ile Ala Met Leu Leu His Thr Asp Gly Ala His Glu Arg Pro Gly Gly
    210                 215                 220

Asp Ala Thr Val Thr Ile Ser His Arg Tyr Thr Pro Lys Glu Gln Leu
225                 230                 235                 240

Lys Lys His Thr Ile Leu Ala Asp Ile Val Ile Ser Ala Ala Gly Ile
                245                 250                 255

Pro Asn Leu Ile Thr Ala Asp Met Ile Lys Glu Gly Ala Ala Val Ile
            260                 265                 270

Asp Val Gly Ile Asn Arg Val His Asp Pro Val Thr Ala Lys Pro Lys
        275                 280                 285

Leu Val Gly Asp Val Asp Phe Glu Gly Val Arg Gln Lys Ala Gly Tyr
    290                 295                 300

Ile Thr Pro Val Pro Gly Gly Val Gly Pro Met Thr Val Ala Met Leu
305                 310                 315                 320

Met Lys Asn Thr Ile Ile Ala Ala Lys Lys Val Leu Arg Leu Glu Glu
                325                 330                 335

Arg Glu Val Leu Lys Ser Lys Glu Leu Gly Val Ala Thr Asn
            340                 345                 350

<210> SEQ ID NO 3
<211> LENGTH: 364
<212> TYPE: PRT
<213> ORGANISM: Escherichia coli

<400> SEQUENCE: 3

Met Ala Gln Gln Thr Pro Leu Tyr Glu Gln His Thr Leu Cys Gly Ala
1               5                   10                  15

Arg Met Val Asp Phe His Gly Trp Met Met Pro Leu His Tyr Gly Ser
            20                  25                  30

Gln Ile Asp Glu His His Ala Val Arg Thr Asp Ala Gly Met Phe Asp
        35                  40                  45

Val Ser His Met Thr Ile Val Asp Leu His Gly Ser Arg Thr Arg Glu
    50                  55                  60

Phe Leu Arg Tyr Leu Leu Ala Asn Asp Val Ala Lys Leu Thr Lys Ser
65                  70                  75                  80

Gly Lys Ala Leu Tyr Ser Gly Met Leu Asn Ala Ser Gly Gly Val Ile
                85                  90                  95

Asp Asp Leu Ile Val Tyr Tyr Phe Thr Glu Asp Phe Phe Arg Leu Val
            100                 105                 110

Val Asn Ser Ala Thr Arg Glu Lys Asp Leu Ser Trp Ile Thr Gln His
        115                 120                 125

Ala Glu Pro Phe Gly Ile Glu Ile Thr Val Arg Asp Asp Leu Ser Met
    130                 135                 140

Ile Ala Val Gln Gly Pro Asn Ala Gln Ala Lys Ala Ala Thr Leu Phe
145                 150                 155                 160

Asn Asp Ala Gln Arg Gln Ala Val Glu Gly Met Lys Pro Phe Phe Gly
                165                 170                 175

Val Gln Ala Gly Asp Leu Phe Ile Ala Thr Thr Gly Tyr Thr Gly Glu
            180                 185                 190

Ala Gly Tyr Glu Ile Ala Leu Pro Asn Glu Lys Ala Ala Asp Phe Trp
        195                 200                 205

Arg Ala Leu Val Glu Ala Gly Val Lys Pro Cys Gly Leu Gly Ala Arg
    210                 215                 220

Asp Thr Leu Arg Leu Glu Ala Gly Met Asn Leu Tyr Ser Gln Glu Met
225                 230                 235                 240

Asp Glu Thr Ile Ser Pro Leu Ala Ala Asn Met Gly Trp Thr Ile Ala
                245                 250                 255

Trp Glu Pro Ala Asp Arg Asp Phe Ile Gly Arg Glu Ala Leu Glu Ala
            260                 265                 270

Gln Arg Glu His Gly Thr Glu Lys Leu Val Gly Leu Val Met Thr Glu
        275                 280                 285

Lys Gly Val Leu Arg Asn Glu Leu Pro Val Arg Phe Thr Asp Ala Gln
    290                 295                 300

Gly Asn Gln His Glu Gly Ile Ile Thr Ser Gly Thr Phe Ser Pro Thr
305                 310                 315                 320

Leu Gly Tyr Ser Ile Ala Leu Ala Arg Val Pro Glu Gly Ile Gly Glu
                325                 330                 335

Thr Ala Ile Val Gln Ile Arg Asn Arg Glu Met Pro Val Lys Val Thr
            340                 345                 350

Lys Pro Val Phe Val Arg Asn Gly Lys Ala Val Ala

<210> SEQ ID NO 4
<211> LENGTH: 495
<212> TYPE: PRT
<213> ORGANISM: Escherichia coli

<400> SEQUENCE: 4

```
Met Asp Asn Gly Arg His Lys Lys Asn Val Arg Pro Ala Gly Asp Lys
1               5                   10                  15

Tyr Ile Glu Val Met Met Ser Thr Glu Ile Lys Thr Gln Val Val Val
            20                  25                  30

Leu Gly Ala Gly Pro Ala Gly Tyr Ser Ala Ala Phe Arg Cys Ala Asp
        35                  40                  45

Leu Gly Leu Glu Thr Val Ile Val Glu Arg Tyr Asn Thr Leu Gly Gly
    50                  55                  60

Val Cys Leu Asn Val Gly Cys Ile Pro Ser Lys Ala Leu Leu His Val
65                  70                  75                  80

Ala Lys Val Ile Glu Glu Ala Lys Ala Leu Ala Glu His Gly Ile Val
                85                  90                  95

Phe Gly Glu Pro Lys Thr Asp Ile Asp Lys Ile Arg Thr Trp Lys Glu
            100                 105                 110

Lys Val Ile Asn Gln Leu Thr Gly Gly Leu Ala Gly Met Ala Lys Gly
        115                 120                 125

Arg Lys Val Lys Val Val Asn Gly Leu Gly Lys Phe Thr Gly Ala Asn
    130                 135                 140

Thr Leu Glu Val Glu Gly Glu Asn Gly Lys Thr Val Ile Asn Phe Asp
145                 150                 155                 160

Asn Ala Ile Ile Ala Ala Gly Ser Arg Pro Ile Gln Leu Pro Phe Ile
                165                 170                 175

Pro His Glu Asp Pro Arg Ile Trp Asp Ser Thr Asp Ala Leu Glu Leu
            180                 185                 190

Lys Glu Val Pro Glu Arg Leu Leu Val Met Gly Gly Gly Ile Ile Gly
        195                 200                 205

Leu Glu Met Gly Thr Val Tyr His Ala Leu Gly Ser Gln Ile Asp Val
    210                 215                 220

Val Glu Met Phe Asp Gln Val Ile Pro Ala Ala Asp Lys Asp Ile Val
225                 230                 235                 240

Lys Val Phe Thr Lys Arg Ile Ser Lys Lys Phe Asn Leu Met Leu Glu
                245                 250                 255

Thr Lys Val Thr Ala Val Glu Ala Lys Glu Asp Gly Ile Tyr Val Thr
            260                 265                 270

Met Glu Gly Lys Lys Ala Pro Ala Glu Pro Gln Arg Tyr Asp Ala Val
        275                 280                 285

Leu Val Ala Ile Gly Arg Val Pro Asn Gly Lys Asn Leu Asp Ala Gly
    290                 295                 300

Lys Ala Gly Val Glu Val Asp Asp Arg Gly Phe Ile Arg Val Asp Lys
305                 310                 315                 320

Gln Leu Arg Thr Asn Val Pro His Ile Phe Ala Ile Gly Asp Ile Val
                325                 330                 335

Gly Gln Pro Met Leu Ala His Lys Gly Val His Glu Gly His Val Ala
            340                 345                 350

Ala Glu Val Ile Ala Gly Lys Lys His Tyr Phe Asp Pro Lys Val Ile
        355                 360                 365
```

-continued

```
Pro Ser Ile Ala Tyr Thr Glu Pro Glu Val Ala Trp Val Gly Leu Thr
    370                 375                 380

Glu Lys Glu Ala Lys Glu Lys Gly Ile Ser Tyr Glu Thr Ala Thr Phe
385                 390                 395                 400

Pro Trp Ala Ala Ser Gly Arg Ala Ile Ala Ser Asp Cys Ala Asp Gly
                405                 410                 415

Met Thr Lys Leu Ile Phe Asp Lys Glu Ser His Arg Val Ile Gly Gly
                420                 425                 430

Ala Ile Val Gly Thr Asn Gly Gly Glu Leu Leu Gly Glu Ile Gly Leu
            435                 440                 445

Ala Ile Glu Met Gly Cys Asp Ala Glu Asp Ile Ala Leu Thr Ile His
        450                 455                 460

Ala His Pro Thr Leu His Glu Ser Val Gly Leu Ala Ala Glu Val Phe
465                 470                 475                 480

Glu Gly Ser Ile Thr Asp Leu Pro Asn Pro Lys Ala Lys Lys Lys
                485                 490                 495

<210> SEQ ID NO 5
<211> LENGTH: 957
<212> TYPE: PRT
<213> ORGANISM: Escherichia coli

<400> SEQUENCE: 5

Met Thr Gln Thr Leu Ser Gln Leu Glu Asn Ser Gly Ala Phe Ile Glu
1               5                   10                  15

Arg His Ile Gly Pro Asp Ala Gln Gln Gln Glu Met Leu Asn Ala
                20                  25                  30

Val Gly Ala Gln Ser Leu Asn Ala Leu Thr Gly Gln Ile Val Pro Lys
            35                  40                  45

Asp Ile Gln Leu Ala Thr Pro Pro Gln Val Gly Ala Pro Ala Thr Glu
        50                  55                  60

Tyr Ala Ala Leu Ala Glu Leu Lys Ala Ile Ala Ser Arg Asn Lys Arg
65                  70                  75                  80

Phe Thr Ser Tyr Ile Gly Met Gly Tyr Thr Ala Val Gln Leu Pro Pro
                85                  90                  95

Val Ile Leu Arg Asn Met Leu Glu Asn Pro Gly Trp Tyr Thr Ala Tyr
                100                 105                 110

Thr Pro Tyr Gln Pro Glu Val Ser Gln Gly Arg Leu Glu Ala Leu Leu
            115                 120                 125

Asn Phe Gln Gln Val Thr Leu Asp Leu Thr Gly Leu Asp Met Ala Ser
        130                 135                 140

Ala Ser Leu Leu Asp Glu Ala Thr Ala Ala Glu Ala Met Ala Met
145                 150                 155                 160

Ala Lys Arg Val Ser Lys Leu Lys Asn Ala Asn Arg Phe Phe Val Ala
                165                 170                 175

Ser Asp Val His Pro Gln Thr Leu Asp Val Val Arg Thr Arg Ala Glu
                180                 185                 190

Thr Phe Gly Phe Glu Val Ile Val Asp Asp Ala Gln Lys Val Leu Asp
            195                 200                 205

His Gln Asp Val Phe Gly Val Leu Leu Gln Gln Val Gly Thr Thr Gly
        210                 215                 220

Glu Ile His Asp Tyr Thr Ala Leu Ile Ser Glu Leu Lys Ser Arg Lys
225                 230                 235                 240

Ile Val Val Ser Val Ala Ala Asp Ile Met Ala Leu Val Leu Leu Thr
                245                 250                 255
```

```
Ala Pro Gly Lys Gln Gly Ala Asp Ile Val Phe Gly Ser Ala Gln Arg
            260                 265                 270

Phe Gly Val Pro Met Gly Tyr Gly Pro His Ala Ala Phe Phe Ala
        275                 280                 285

Ala Lys Asp Glu Tyr Lys Arg Ser Met Pro Gly Arg Ile Ile Gly Val
    290                 295                 300

Ser Lys Asp Ala Ala Gly Asn Thr Ala Leu Arg Met Ala Met Gln Thr
305                 310                 315                 320

Arg Glu Gln His Ile Arg Arg Glu Lys Ala Asn Ser Asn Ile Cys Thr
                325                 330                 335

Ser Gln Val Leu Leu Ala Asn Ile Ala Ser Leu Tyr Ala Val Tyr His
            340                 345                 350

Gly Pro Ile Gly Leu Lys Arg Ile Ala Asn Arg Ile His Arg Leu Thr
        355                 360                 365

Asp Ile Leu Ala Ala Gly Leu Gln Gln Lys Gly Leu Lys Leu Arg His
    370                 375                 380

Ala His Tyr Phe Asp Thr Leu Cys Val Glu Val Ala Asp Lys Ala Gly
385                 390                 395                 400

Val Leu Thr Arg Ala Glu Ala Glu Ile Asn Leu Arg Ser Asp Ile
                405                 410                 415

Leu Asn Ala Val Gly Ile Thr Leu Asp Glu Thr Thr Thr Arg Glu Asn
            420                 425                 430

Val Met Gln Leu Phe Asn Val Leu Leu Gly Asp Asn His Gly Leu Asp
            435                 440                 445

Ile Asp Thr Leu Asp Lys Asp Val Ala His Asp Ser Arg Ser Ile Gln
    450                 455                 460

Pro Ala Met Leu Arg Asp Asp Glu Ile Leu Thr His Pro Val Phe Asn
465                 470                 475                 480

Arg Tyr His Ser Glu Thr Glu Met Met Arg Tyr Met His Ser Leu Glu
                485                 490                 495

Arg Lys Asp Leu Ala Leu Asn Gln Ala Met Ile Pro Leu Gly Ser Cys
            500                 505                 510

Thr Met Lys Leu Asn Ala Ala Glu Met Ile Pro Ile Thr Trp Pro
            515                 520                 525

Glu Phe Ala Glu Leu His Pro Phe Cys Pro Glu Gln Ala Glu Gly
        530                 535                 540

Tyr Gln Gln Met Ile Ala Gln Leu Ala Asp Trp Leu Val Lys Leu Thr
545                 550                 555                 560

Gly Tyr Asp Ala Val Cys Met Gln Pro Asn Ser Gly Ala Gln Gly Glu
                565                 570                 575

Tyr Ala Gly Leu Leu Ala Ile Arg His Tyr His Glu Ser Arg Asn Glu
            580                 585                 590

Gly His Arg Asp Ile Cys Leu Ile Pro Ala Ser Ala His Gly Thr Asn
        595                 600                 605

Pro Ala Ser Ala His Met Ala Gly Met Gln Val Val Val Ala Cys
610                 615                 620

Asp Lys Asn Gly Asn Ile Asp Leu Thr Asp Leu Arg Ala Lys Ala Glu
625                 630                 635                 640

Gln Ala Gly Asp Asn Leu Ser Cys Ile Met Val Thr Tyr Pro Ser Thr
                645                 650                 655

His Gly Val Tyr Glu Glu Thr Ile Arg Glu Val Cys Glu Val Val His
            660                 665                 670
```

```
Gln Phe Gly Gly Gln Val Tyr Leu Asp Gly Ala Asn Met Asn Ala Gln
            675                 680                 685

Val Gly Ile Thr Ser Pro Gly Phe Ile Gly Ala Asp Val Ser His Leu
        690                 695                 700

Asn Leu His Lys Thr Phe Cys Ile Pro His Gly Gly Gly Pro Gly
705                 710                 715                 720

Met Gly Pro Ile Gly Val Lys Ala His Leu Ala Pro Phe Val Pro Gly
                725                 730                 735

His Ser Val Val Gln Ile Glu Gly Met Leu Thr Arg Gln Gly Ala Val
            740                 745                 750

Ser Ala Ala Pro Phe Gly Ser Ala Ser Ile Leu Pro Ile Ser Trp Met
        755                 760                 765

Tyr Ile Arg Met Met Gly Ala Glu Gly Leu Lys Lys Ala Ser Gln Val
        770                 775                 780

Ala Ile Leu Asn Ala Asn Tyr Ile Ala Ser Arg Leu Gln Asp Ala Phe
785                 790                 795                 800

Pro Val Leu Tyr Thr Gly Arg Asp Gly Arg Val Ala His Glu Cys Ile
                805                 810                 815

Leu Asp Ile Arg Pro Leu Lys Glu Glu Thr Gly Ile Ser Glu Leu Asp
            820                 825                 830

Ile Ala Lys Arg Leu Ile Asp Tyr Gly Phe His Ala Pro Thr Met Ser
        835                 840                 845

Phe Pro Val Ala Gly Thr Leu Met Val Glu Pro Thr Glu Ser Glu Ser
        850                 855                 860

Lys Val Glu Leu Asp Arg Phe Ile Asp Ala Met Leu Ala Ile Arg Ala
865                 870                 875                 880

Glu Ile Asp Gln Val Lys Ala Gly Val Trp Pro Leu Glu Asp Asn Pro
                885                 890                 895

Leu Val Asn Ala Pro His Ile Gln Asn Glu Leu Val Ala Glu Trp Ala
            900                 905                 910

His Pro Tyr Ser Arg Glu Val Ala Val Phe Pro Ala Gly Val Ala Asp
        915                 920                 925

Lys Tyr Trp Pro Thr Val Lys Arg Leu Asp Asp Val Tyr Gly Asp Arg
        930                 935                 940

Asn Leu Phe Cys Ser Cys Val Pro Ile Ser Glu Tyr Gln
945                 950                 955

<210> SEQ ID NO 6
<211> LENGTH: 417
<212> TYPE: PRT
<213> ORGANISM: Escherichia coli

<400> SEQUENCE: 6

Met Leu Lys Arg Glu Met Asn Ile Ala Asp Tyr Asp Ala Glu Leu Trp
1               5                   10                  15

Gln Ala Met Glu Gln Glu Lys Val Arg Gln Glu Glu His Ile Glu Leu
            20                  25                  30

Ile Ala Ser Glu Asn Tyr Thr Ser Pro Arg Val Met Gln Ala Gln Gly
        35                  40                  45

Ser Gln Leu Thr Asn Lys Tyr Ala Glu Gly Tyr Pro Gly Lys Arg Tyr
    50                  55                  60

Tyr Gly Gly Cys Glu Tyr Val Asp Ile Val Glu Gln Leu Ala Ile Asp
65                  70                  75                  80

Arg Ala Lys Glu Leu Phe Gly Ala Asp Tyr Ala Asn Val Gln Pro His
                85                  90                  95
```

Ser Gly Ser Gln Ala Asn Phe Ala Val Tyr Thr Ala Leu Leu Glu Pro
            100                 105                 110

Gly Asp Thr Val Leu Gly Met Asn Leu Ala His Gly His Leu Thr
            115                 120                 125

His Gly Ser Pro Val Asn Phe Ser Gly Lys Leu Tyr Asn Ile Val Pro
            130                 135                 140

Tyr Gly Ile Asp Ala Thr Gly His Ile Asp Tyr Ala Asp Leu Glu Lys
145                 150                 155                 160

Gln Ala Lys Glu His Lys Pro Lys Met Ile Ile Gly Gly Phe Ser Ala
            165                 170                 175

Tyr Ser Gly Val Val Asp Trp Ala Lys Met Arg Glu Ile Ala Asp Ser
            180                 185                 190

Ile Gly Ala Tyr Leu Phe Val Asp Met Ala His Val Ala Gly Leu Val
            195                 200                 205

Ala Ala Gly Val Tyr Pro Asn Pro Val Pro His Ala His Val Val Thr
210                 215                 220

Thr Thr Thr His Lys Thr Leu Ala Gly Pro Arg Gly Gly Leu Ile Leu
225                 230                 235                 240

Ala Lys Gly Gly Ser Glu Glu Leu Tyr Lys Lys Leu Asn Ser Ala Val
            245                 250                 255

Phe Pro Gly Gly Gln Gly Gly Pro Leu Met His Val Ile Ala Gly Lys
            260                 265                 270

Ala Val Ala Leu Lys Glu Ala Met Glu Pro Glu Phe Lys Thr Tyr Gln
            275                 280                 285

Gln Gln Val Ala Lys Asn Ala Lys Ala Met Val Glu Val Phe Leu Glu
            290                 295                 300

Arg Gly Tyr Lys Val Val Ser Gly Gly Thr Asp Asn His Leu Phe Leu
305                 310                 315                 320

Val Asp Leu Val Asp Lys Asn Leu Thr Gly Lys Glu Ala Asp Ala Ala
            325                 330                 335

Leu Gly Arg Ala Asn Ile Thr Val Asn Lys Asn Ser Val Pro Asn Asp
            340                 345                 350

Pro Lys Ser Pro Phe Val Thr Ser Gly Ile Arg Val Gly Thr Pro Ala
            355                 360                 365

Ile Thr Arg Arg Gly Phe Lys Glu Ala Glu Ala Lys Glu Leu Ala Gly
370                 375                 380

Trp Met Cys Asp Val Leu Asp Ser Ile Asn Asp Glu Ala Val Ile Glu
385                 390                 395                 400

Arg Ile Lys Gly Lys Val Leu Asp Ile Cys Ala Arg Tyr Pro Val Tyr
            405                 410                 415

Ala

<210> SEQ ID NO 7
<211> LENGTH: 454
<212> TYPE: PRT
<213> ORGANISM: Escherichia coli

<400> SEQUENCE: 7

Met Ile Ser Leu Phe Asp Met Phe Lys Val Gly Ile Gly Pro Ser Ser
1               5                   10                  15

Ser His Thr Val Gly Pro Met Lys Ala Gly Lys Gln Phe Val Asp Asp
            20                  25                  30

Leu Val Glu Lys Gly Leu Leu Asp Ser Val Thr Arg Val Ala Val Asp
            35                  40                  45

```
Val Tyr Gly Ser Leu Ser Leu Thr Gly Lys Gly His His Thr Asp Ile
 50                  55                  60
Ala Ile Ile Met Gly Leu Ala Gly Asn Glu Pro Ala Thr Val Asp Ile
 65                  70                  75                  80
Asp Ser Ile Pro Gly Phe Ile Arg Asp Val Glu Glu Arg Glu Arg Leu
                 85                  90                  95
Leu Leu Ala Gln Gly Arg His Glu Val Asp Phe Pro Arg Asp Asn Gly
                100                 105                 110
Met Arg Phe His Asn Gly Asn Leu Pro Leu His Glu Asn Gly Met Gln
            115                 120                 125
Ile His Ala Tyr Asn Gly Asp Glu Val Val Tyr Ser Lys Thr Tyr Tyr
        130                 135                 140
Ser Ile Gly Gly Gly Phe Ile Val Asp Glu Glu His Phe Gly Gln Asp
145                 150                 155                 160
Ala Ala Asn Glu Val Ser Val Pro Tyr Pro Phe Lys Ser Ala Thr Glu
                165                 170                 175
Leu Leu Ala Tyr Cys Asn Glu Thr Gly Tyr Ser Leu Ser Gly Leu Ala
                180                 185                 190
Met Gln Asn Glu Leu Ala Leu His Ser Lys Lys Glu Ile Asp Glu Tyr
            195                 200                 205
Phe Ala His Val Trp Gln Thr Met Gln Ala Cys Ile Asp Arg Gly Met
        210                 215                 220
Asn Thr Glu Gly Val Leu Pro Gly Pro Leu Arg Val Pro Arg Arg Ala
225                 230                 235                 240
Ser Ala Leu Arg Arg Met Leu Val Ser Ser Asp Lys Leu Ser Asn Asp
                245                 250                 255
Pro Met Asn Val Ile Asp Trp Val Asn Met Phe Ala Leu Ala Val Asn
                260                 265                 270
Glu Glu Asn Ala Ala Gly Gly Arg Val Val Thr Ala Pro Thr Asn Gly
            275                 280                 285
Ala Cys Gly Ile Val Pro Ala Val Leu Ala Tyr Tyr Asp His Phe Ile
        290                 295                 300
Glu Ser Val Ser Pro Asp Ile Tyr Thr Arg Tyr Phe Met Ala Ala Gly
305                 310                 315                 320
Ala Ile Gly Ala Leu Tyr Lys Met Asn Ala Ser Ile Ser Gly Ala Glu
                325                 330                 335
Val Gly Cys Gln Gly Glu Val Gly Val Ala Cys Ser Met Ala Ala Ala
                340                 345                 350
Gly Leu Ala Glu Leu Leu Gly Gly Ser Pro Glu Gln Val Cys Val Ala
            355                 360                 365
Ala Glu Ile Gly Met Glu His Asn Leu Gly Leu Thr Cys Asp Pro Val
        370                 375                 380
Ala Gly Gln Val Gln Val Pro Cys Ile Glu Arg Asn Ala Ile Ala Ser
385                 390                 395                 400
Val Lys Ala Ile Asn Ala Ala Arg Met Ala Leu Arg Arg Thr Ser Ala
                405                 410                 415
Pro Arg Val Ser Leu Asp Lys Val Ile Glu Thr Met Tyr Glu Thr Gly
                420                 425                 430
Lys Asp Met Asn Ala Lys Tyr Arg Glu Thr Ser Arg Gly Gly Leu Ala
            435                 440                 445
Ile Lys Val Gln Cys Asp
    450
```

<210> SEQ ID NO 8
<211> LENGTH: 381
<212> TYPE: PRT
<213> ORGANISM: Deinococcus maricopensis

<400> SEQUENCE: 8

```
Met Leu Pro Glu His Ser Glu His Thr Leu Thr Pro Gly Pro Thr
1               5                   10                  15

Pro Leu His Pro His Ala Gln His Ala Leu Thr Arg Pro Met Leu Gly
            20                  25                  30

His Met Asp Pro Asp Val Phe Ala Leu Asn Arg Glu Ile Gln Ala Asp
        35                  40                  45

Leu Arg Thr Met Tyr Gly Ala Thr Pro Asp Thr Phe Thr Ala Leu Leu
    50                  55                  60

Ala Gly Thr Gly Ser Leu Gly Met Glu Ala Gly Phe Ala Asn Leu Val
65                  70                  75                  80

Glu Pro Gly Asp Thr Val Val Val Cys Ala Asn Gly Ser Phe Gly Ala
                85                  90                  95

Arg Met Ala Glu Met Ala Glu Arg Tyr Gly Ala His Val Arg Thr Val
            100                 105                 110

Thr Ala Pro Leu Gly Glu Pro Ile Asp Pro Glu Gln Val Ala Ala His
        115                 120                 125

Leu Asp Gly Ala Arg Met Val Ala Val Val His Gly Glu Thr Ser Thr
    130                 135                 140

Gly Val Leu Asn Pro Val Pro Ala Ile Ala Arg Leu Ala Arg Glu Ser
145                 150                 155                 160

Gly Ala Leu Leu Thr Val Asp Ala Val Thr Thr Ala Gly Met Glu Pro
                165                 170                 175

Phe His Ala Glu Ala Trp Gly Val Asp Tyr Ala Tyr Thr Gly Ala Gln
            180                 185                 190

Lys Cys Leu Ser Ala Pro Pro Gly Val Ala Pro Val Met Ile Ser Asp
        195                 200                 205

Arg Ala Phe Asp Arg Phe His Ala Arg Arg Glu Arg Thr Pro Leu Trp
    210                 215                 220

Tyr Cys Asp Phe Asp Gly Leu Arg Asp Tyr Trp Glu Arg Gln Ser Tyr
225                 230                 235                 240

His His Thr Val Pro Val Asn Leu His Phe Ala Leu His Ala Ala Leu
                245                 250                 255

Arg Ala Ala Leu Asp Glu Gly Leu Thr Thr Arg Arg Asp Arg Val Arg
            260                 265                 270

His Leu Ser Gly Ala Ile Gln Ala Thr Leu Ala Pro Leu Gly Phe Thr
        275                 280                 285

Pro Phe Val Arg Asp Pro Ala Arg Leu Pro Val Leu Ala Leu
    290                 295                 300

Arg Leu Pro Asp Gly Leu Asp Asp Ala Gly Val Arg Arg Ala Leu Arg
305                 310                 315                 320

Glu Arg His Ile Ser Ile Thr Gly Gly Leu Gly Pro Thr Ala Gly Leu
                325                 330                 335

Ile Trp Arg Leu Gly Leu Met Gly Glu Ala Ala Arg Pro Ala Pro Tyr
            340                 345                 350

Arg Thr Leu Met Thr Ala Leu Glu Asp Leu Leu Gly Ala Pro Gly Leu
        355                 360                 365

Arg Ala Arg Phe Asp Asp Ala Leu Ala Ala Val Pro Ala
    370                 375                 380
```

<210> SEQ ID NO 9
<211> LENGTH: 328
<212> TYPE: PRT
<213> ORGANISM: Escherichia coli

<400> SEQUENCE: 9

Met Glu Arg Ser Met Lys Pro Ser Val Ile Leu Tyr Lys Ala Leu Pro
1               5                   10                  15

Asp Asp Leu Leu Gln Arg Leu Gln Glu His Phe Thr Val His Gln Val
            20                  25                  30

Ala Asn Leu Ser Pro Gln Thr Val Glu Gln Asn Ala Ala Ile Phe Ala
        35                  40                  45

Glu Ala Glu Gly Leu Leu Gly Ser Asn Glu Asn Val Asp Ala Ala Leu
    50                  55                  60

Leu Glu Lys Met Pro Lys Leu Arg Ala Thr Ser Thr Ile Ser Val Gly
65                  70                  75                  80

Tyr Asp Asn Phe Asp Val Asp Ala Leu Thr Ala Arg Lys Ile Leu Leu
                85                  90                  95

Met His Thr Pro Thr Val Leu Thr Glu Thr Val Ala Asp Thr Leu Met
            100                 105                 110

Ala Leu Val Leu Ser Thr Ala Arg Arg Val Val Glu Val Ala Glu Arg
        115                 120                 125

Val Lys Ala Gly Glu Trp Thr Ala Ser Ile Gly Pro Asp Trp Tyr Gly
    130                 135                 140

Thr Asp Val His His Lys Thr Leu Gly Ile Val Gly Met Gly Arg Ile
145                 150                 155                 160

Gly Met Ala Leu Ala Gln Arg Ala His Phe Gly Phe Asn Met Pro Ile
                165                 170                 175

Leu Tyr Asn Ala Arg Arg His His Lys Glu Ala Glu Glu Arg Phe Asn
            180                 185                 190

Ala Arg Tyr Cys Asn Leu Asp Thr Leu Leu Gln Glu Ser Asp Phe Val
        195                 200                 205

Cys Leu Ile Leu Pro Leu Thr Asp Glu Thr His His Leu Phe Gly Ala
    210                 215                 220

Glu Gln Phe Ala Lys Met Lys Ser Ser Ala Ile Phe Ile Asn Ala Gly
225                 230                 235                 240

Arg Gly Pro Val Val Asp Glu Asn Ala Leu Ile Ala Ala Leu Gln Lys
                245                 250                 255

Gly Glu Ile His Ala Ala Gly Leu Asp Val Phe Glu Gln Glu Pro Leu
            260                 265                 270

Ser Val Asp Ser Pro Leu Leu Ser Met Ala Asn Val Val Ala Val Pro
        275                 280                 285

His Ile Gly Ser Ala Thr His Glu Thr Arg Tyr Gly Met Ala Ala Cys
    290                 295                 300

Ala Val Asp Asn Leu Ile Asp Ala Leu Gln Gly Lys Val Glu Lys Asn
305                 310                 315                 320

Cys Val Asn Pro His Val Ala Asp
                325

<210> SEQ ID NO 10
<211> LENGTH: 381
<212> TYPE: PRT
<213> ORGANISM: Desulfobacca acetoxidans

<400> SEQUENCE: 10

-continued

```
Met Lys Lys His Tyr Leu Leu Ala Pro Gly Pro Thr Pro Val Ser Pro
1               5                   10                  15

Glu Thr Leu Leu Ala Met Ala Thr Pro Ile Ile His His Arg Ser Pro
            20                  25                  30

Gln Phe Ala Glu Val Val Ala Glu Cys Arg Val Gly Leu Lys Tyr Leu
        35                  40                  45

Phe Gln Thr Lys Gln Glu Val Leu Ile Leu Ala Ser Thr Gly Thr Gly
    50                  55                  60

Ala Met Glu Gly Ala Ile Thr Asn Thr Leu Ser Pro Gly Asp Thr Ala
65                  70                  75                  80

Leu Val Val Arg Gly Gly Lys Phe Gly Glu Arg Trp Gly Glu Ile Cys
                85                  90                  95

Ala Ala Tyr Gly Val Asn Phe Glu Ala Ile Asp Val Glu Trp Gly Arg
            100                 105                 110

Ala Val Gln Val Ala Asp Val Ala Ala Lys Leu Lys Ala Asn Pro Ala
        115                 120                 125

Ile Lys Ala Val Cys Ile Gln Ala His Glu Thr Ser Thr Gly Val Asn
130                 135                 140

His Pro Val Lys Glu Leu Ala Glu Leu Thr Lys Ser Leu Pro Gly Thr
145                 150                 155                 160

Leu Leu Leu Val Asp Ala Ile Ser Ala Leu Gly Ala Phe Glu Leu Pro
                165                 170                 175

Met Asp Ala Trp Gly Ile Asp Ile Met Val Ala Gly Ser Gln Lys Ala
            180                 185                 190

Met Met Leu Pro Pro Gly Leu Ala Phe Ala Cys Leu Ser Glu Lys Ala
        195                 200                 205

Trp Glu Phe Thr Lys Thr Ala Thr Cys Asn Lys Tyr Tyr Phe Asn Phe
    210                 215                 220

Ser Lys Glu Leu Lys Asn Ile Gln Lys Asn Thr Gly Ala Tyr Thr Ser
225                 230                 235                 240

Ala Val Ser Leu Val Met Gly Leu Arg Asp Val Leu Arg Tyr Phe Lys
                245                 250                 255

Glu Ala Thr Leu Glu Lys Ile Phe Ala Glu His Gln Leu Met Ser Lys
            260                 265                 270

Ala Thr Lys Ala Ala Val Lys Ala Leu Gly Leu Glu Leu Phe Ser Gln
        275                 280                 285

Glu Gly Ala Ser Asp Ala Leu Thr Ala Val Arg Ala Pro Ala Gly Val
    290                 295                 300

Asp Gly Gln Asp Val Val Lys Leu Leu Arg Asp Lys Tyr Gly Ile Met
305                 310                 315                 320

Ile Ala Gly Gly Gln Ala Glu Ala Lys Gly Lys Ile Phe Arg Ile Ala
                325                 330                 335

His Met Gly Tyr Ile Gly Asn Phe Asp Ile Val Met Ile Ile Ala Ala
            340                 345                 350

Leu Glu Val Val Leu Asn Glu Leu Gly Tyr Lys Ala Pro Tyr Gly Ala
        355                 360                 365

Gly Val Lys Ala Ala Glu Glu Val Leu Phe Gly Gly Ala
    370                 375                 380

<210> SEQ ID NO 11
<211> LENGTH: 249
<212> TYPE: PRT
<213> ORGANISM: Agrobacterium tumefaciens
```

<400> SEQUENCE: 11

```
Met Ser Gly Thr Ile Leu Ile Thr Gly Ala Thr Ser Gly Phe Gly Gln
1               5                   10                  15

Ala Thr Ala Gln Arg Phe Val Lys Glu Gly Trp Lys Val Ile Gly Thr
            20                  25                  30

Gly Arg Arg Ala Glu Arg Leu Glu Ala Leu Ser Ala Glu Leu Gly Ser
        35                  40                  45

Ala Phe His Gly Val Ala Phe Asp Ile Thr Asp Glu Glu Ala Thr Lys
    50                  55                  60

Lys Ala Leu Ala Gly Leu Pro Asp Gly Phe Arg Asp Ile Asp Ile Leu
65                  70                  75                  80

Val Asn Asn Ala Gly Leu Ala Leu Gly Thr Ala Pro Ala Pro Gln Val
                85                  90                  95

Pro Leu Lys Asp Trp Gln Thr Met Val Asp Thr Asn Ile Thr Gly Leu
            100                 105                 110

Leu Asn Val Thr His His Leu Leu Pro Thr Leu Ile Glu Arg Lys Gly
        115                 120                 125

Ile Val Ile Asn Leu Ser Ser Val Ala Ala His Tyr Pro Tyr Leu Gly
    130                 135                 140

Gly Asn Val Tyr Gly Gly Thr Lys Ala Phe Leu Arg Gln Phe Ser Leu
145                 150                 155                 160

Gly Leu Arg Ser Asp Leu His Gly Lys Gly Val Arg Val Thr Ser Ile
                165                 170                 175

Glu Pro Gly Met Cys Glu Thr Glu Phe Thr Leu Val Arg Thr Gly Gly
            180                 185                 190

Asn Gln Glu Ala Ser Asp Asn Leu Tyr Lys Gly Val Asn Pro Ile Thr
        195                 200                 205

Ala Asp Asp Ile Ala Asn Thr Ile His Trp Val Ala Ser Gln Pro Lys
    210                 215                 220

His Ile Asn Ile Asn Ser Leu Glu Leu Met Pro Val Asn Gln Ser Phe
225                 230                 235                 240

Ala Gly Phe Gln Val Tyr Arg Glu Ser
                245
```

<210> SEQ ID NO 12
<211> LENGTH: 364
<212> TYPE: PRT
<213> ORGANISM: Candida boidinii

<400> SEQUENCE: 12

```
Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110
```

```
Leu Glu Val Thr Gly Ser Asn Val Ser Val Ala Glu His Val Val
        115                 120                 125
Met Thr Met Leu Val Leu Val Arg Asn Phe Val Pro Ala His Glu Gln
130                 135                 140
Ile Ile Asn His Asp Trp Glu Val Ala Ala Ile Ala Lys Asp Ala Tyr
145                 150                 155                 160
Asp Ile Glu Gly Lys Thr Ile Ala Thr Ile Gly Ala Gly Arg Ile Gly
                165                 170                 175
Tyr Arg Val Leu Glu Arg Leu Leu Pro Phe Asn Pro Lys Glu Leu Leu
            180                 185                 190
Tyr Tyr Asp Tyr Gln Ala Leu Pro Lys Glu Ala Glu Lys Val Gly
        195                 200                 205
Ala Arg Arg Val Glu Asn Ile Glu Glu Leu Val Ala Gln Ala Asp Ile
    210                 215                 220
Val Thr Val Asn Ala Pro Leu His Ala Gly Thr Lys Gly Leu Ile Asn
225                 230                 235                 240
Lys Glu Leu Leu Ser Lys Phe Lys Lys Gly Ala Trp Leu Val Asn Thr
                245                 250                 255
Ala Arg Gly Ala Ile Cys Val Ala Glu Asp Val Ala Ala Ala Leu Glu
            260                 265                 270
Ser Gly Gln Leu Arg Gly Tyr Gly Gly Asp Val Trp Phe Pro Gln Pro
        275                 280                 285
Ala Pro Lys Asp His Pro Trp Arg Asp Met Arg Asn Lys Tyr Gly Ala
    290                 295                 300
Gly Asn Ala Met Thr Pro His Tyr Ser Gly Thr Thr Leu Asp Ala Gln
305                 310                 315                 320
Thr Arg Tyr Ala Glu Gly Thr Lys Asn Ile Leu Glu Ser Phe Phe Thr
                325                 330                 335
Gly Lys Phe Asp Tyr Arg Pro Gln Asp Ile Ile Leu Leu Asn Gly Glu
            340                 345                 350
Tyr Val Thr Lys Ala Tyr Gly Lys His Asp Lys Lys
        355                 360

<210> SEQ ID NO 13
<211> LENGTH: 893
<212> TYPE: PRT
<213> ORGANISM: Moorella thermoacetica
<220> FEATURE:
<221> NAME/KEY: misc_feature
<222> LOCATION: (358)..(358)
<223> OTHER INFORMATION: Selenocysteine

<400> SEQUENCE: 13

Met Val Asn Leu Thr Ile Asp Gly Gln Arg Val Thr Ala Pro Glu Gly
1               5                   10                  15
Met Thr Ile Leu Glu Val Ala Arg Glu Asn Gly Ile His Ile Pro Thr
            20                  25                  30
Leu Cys His His Pro Lys Leu Arg Pro Leu Gly Tyr Cys Arg Leu Cys
        35                  40                  45
Leu Val Asp Ile Glu Gly Ala Ala Lys Pro Met Thr Ala Cys Asn Thr
    50                  55                  60
Pro Val Ala Glu Gly Met Val Ile Arg Thr Ser Thr Pro Val Ile Glu
65                  70                  75                  80
Glu Met Arg Lys Gly Ile Ile Glu Met Leu Leu Ser Leu His Pro Glu
                85                  90                  95
Asp Cys Leu Thr Cys Glu Lys Ala Gly Asn Cys Gln Leu Gln Asp Cys
```

```
            100                 105                 110
Ala Tyr Thr Tyr Gly Val Lys His Gly Glu Leu Pro Val Lys Arg Glu
            115                 120                 125

Glu Leu Pro Val Leu Lys Glu Asn Pro Phe Ile Val Arg Asp Tyr Asn
        130                 135                 140

Lys Cys Ile Val Cys Gly Arg Cys Val Arg Ala Cys Gln Glu Val Gln
145                 150                 155                 160

Val Gln Arg Val Val Asp Leu Val Gly Lys Gly Ser Ala Ala Arg Val
                165                 170                 175

Gly Ala Thr Lys Ala Gly Ala Glu Val Ser Leu Glu Glu Gly Gly Cys
            180                 185                 190

Val Phe Cys Gly Asn Cys Val Gln Val Cys Pro Val Gly Ala Leu Thr
        195                 200                 205

Glu Lys Ala Gly Leu Gly Gln Gly Arg Glu Trp Glu Phe Lys Lys Val
    210                 215                 220

Arg Ser Ile Cys Ser Tyr Cys Gly Val Gly Cys Asn Leu Thr Leu Tyr
225                 230                 235                 240

Val Lys Asp Gly Lys Val Val Lys Val Arg Gly Tyr Glu Asn Pro Glu
                245                 250                 255

Val Asn Asn Gly Trp Leu Cys Val Lys Gly Arg Phe Gly Phe Asp Tyr
            260                 265                 270

Ile His Asn Pro Asp Arg Ile Thr Arg Pro Leu Ile Arg Glu Gly Asp
        275                 280                 285

Arg Glu Lys Gly Tyr Phe Arg Glu Ala Ser Trp Glu Glu Ala Leu Ala
    290                 295                 300

Leu Val Ser Gln Lys Leu Thr Gln Ile Lys Gly Ser Tyr Gly Ser Glu
305                 310                 315                 320

Ala Leu Gly Phe Leu Cys Ser Ala Lys Cys Thr Asn Glu Glu Asn Tyr
                325                 330                 335

Leu Leu Gln Lys Leu Ala Arg Gly Val Leu Gly Thr Asn Asn Val Asp
            340                 345                 350

His Cys Ala Arg Leu Asn His Ser Ser Thr Val Ala Gly Leu Ala Thr
        355                 360                 365

Thr Phe Gly Ser Gly Ala Met Thr Asn Ser Ile Ala Asp Ile Ala Ser
    370                 375                 380

Ala Asp Cys Ile Phe Val Ile Gly Ser Asn Thr Thr Glu Asn His Pro
385                 390                 395                 400

Val Ile Ala Leu Lys Val Lys Glu Ala Val Arg Arg Gly Ala Arg Leu
                405                 410                 415

Ile Val Ala Asp Pro Arg Arg Ile Glu Leu Val Asn Phe Ser Tyr Leu
            420                 425                 430

Trp Leu Arg Gln Lys Pro Gly Thr Asp Leu Ala Leu Leu Asn Gly Leu
        435                 440                 445

Leu His Val Ile Lys Glu Glu Leu Tyr Asp Lys Glu Phe Ile Ala
    450                 455                 460

Gln Arg Thr Glu Gly Phe Glu Ala Leu Lys Leu Ala Val Glu Glu Tyr
465                 470                 475                 480

Thr Pro Ala Lys Val Ser Glu Val Thr Gly Val Pro Ala Gly Asp Ile
                485                 490                 495

Ile Glu Ala Ala Arg Thr Tyr Ala Arg Gly Pro Ser Ser Thr Ile Leu
            500                 505                 510

Tyr Ala Met Gly Ile Thr Gln His Ile Thr Gly Thr Ala Asn Val Met
        515                 520                 525
```

```
Ala Leu Ala Asn Leu Ala Met Ala Cys Gly Gln Val Gly Lys Glu Gly
            530                 535                 540

Asn Gly Val Asn Pro Leu Arg Gly Gln Ser Asn Val Gln Gly Ala Cys
545                 550                 555                 560

Asp Met Gly Gly Leu Pro Asn Val Leu Pro Gly Tyr Gln Pro Val Thr
            565                 570                 575

Asp Pro Gly Val Arg His Lys Phe Ser Glu Thr Trp Gly Val Pro Asp
            580                 585                 590

Leu Pro Gly Glu Pro Gly Leu Thr Leu Met Glu Met Ala Ala Ala
            595                 600                 605

Gln Glu Gly Lys Leu Lys Gly Met Tyr Ile Leu Gly Glu Asn Pro Val
610                 615                 620

Leu Thr Asp Pro Asp Val Ser His Val Lys Glu Ala Leu Lys Asn Leu
625                 630                 635                 640

Glu Phe Leu Val Val Gln Asp Ile Phe Leu Thr Glu Thr Ala Arg Met
            645                 650                 655

Ala Asp Val Val Leu Pro Gly Ala Ser Phe Ala Glu Lys Glu Gly Thr
            660                 665                 670

Phe Thr Ser Thr Glu Arg Arg Val Gln Leu Leu His Lys Ala Ile Glu
            675                 680                 685

Pro Pro Gly Glu Ala Arg Pro Asp Trp Leu Ile Leu Asn Asp Leu Leu
690                 695                 700

Leu Leu Met Gly Tyr Pro Arg Lys Tyr Ser Ser Pro Gly Glu Ile Met
705                 710                 715                 720

Gln Glu Ile Ala Gly Leu Thr Pro Ser Tyr Ala Gly Ile Thr Tyr Glu
            725                 730                 735

Arg Leu Glu Asp Lys Gly Leu Gln Trp Pro Val Leu Ser Leu Glu His
            740                 745                 750

Pro Gly Thr Pro Val Leu His Arg Glu Lys Phe Ser Arg Gly Tyr Gly
            755                 760                 765

Gln Phe Gln Val Val His Tyr Arg Pro Pro Ala Glu Glu Pro Asp Glu
770                 775                 780

Glu Tyr Pro Phe Leu Phe Thr Thr Gly Arg Asn Leu Tyr His Tyr His
785                 790                 795                 800

Thr Val Ile Ser Arg Lys Ser Arg Gly Leu Glu Glu Met Cys Pro Ala
            805                 810                 815

Pro Val Val Glu Ile Asn Asp Asn Asp Ala Ala Arg Leu Gly Ile Arg
            820                 825                 830

Glu Gly Glu Met Ile Glu Ile Val Ser Arg Arg Gly Lys Val Arg Val
            835                 840                 845

Lys Ala Leu Val Thr Asp Arg Ile Pro Arg Gly Gln Val Phe Met Asn
850                 855                 860

Phe His Phe His Glu Ala Ala Ala Asn Leu Leu Thr Ile Ala Ala Leu
865                 870                 875                 880

Asp Pro Val Ala Lys Ile Pro Ile Ile Lys Pro Val Leu
                885                 890

<210> SEQ ID NO 14
<211> LENGTH: 707
<212> TYPE: PRT
<213> ORGANISM: Moorella thermoacetica

<400> SEQUENCE: 14

Met Gly Glu Val Val Phe Ser Thr Trp Gly Gly Lys Val Val Asp His
```

```
1               5                    10                   15
Arg Gly Gly Pro Ser Gly Gly Pro Ser Trp Ala Gly Glu Phe Gly
                20                  25                  30
Gly Arg Gln Leu Lys Ala Phe Ile Gly Trp Asp Gly Leu Val Val Thr
            35                  40                  45
Asp Pro Ala Val Asp Leu Leu Ala Leu Gln Ala Tyr Tyr Gln Ala
    50                  55                  60
Val Gln Gly Glu Ser Cys Gly Arg Cys Val Pro Cys Arg Val Gly Thr
65                  70                  75                  80
Arg Val Ile Tyr Asn Val Leu Val Arg Ile Ala Gly Gly Glu Gly Leu
                85                  90                  95
Pro Ser Asp Leu Asp Leu Leu Arg Arg Val Ala Trp Ile Val Arg Asp
                100                 105                 110
Gly Ser Leu Cys Glu Leu Gly Gln Ala Gly Ala Lys Ala Val Leu Asp
                115                 120                 125
Phe Leu Asp Tyr Tyr Ser Glu Ala Leu Arg Pro Phe Leu Glu Asp Ser
    130                 135                 140
Gly Arg Val Ala Gly Gly Gln Arg Arg Pro Gly Pro Gly Gly Arg Val
145                 150                 155                 160
Gln Val Leu Ala Ser Gly Arg Val Leu Val Gly Asn Asp Arg Gly Lys
                165                 170                 175
Gly Ala Ala Ala Ser Pro Ala Ala Gly Leu Thr Tyr Lys Pro Phe
                180                 185                 190
Val Thr Ala Pro Cys Leu Lys Arg Cys Pro Ala His Leu Asp Ile Pro
    195                 200                 205
Ala Tyr Ile Asp Ala Ile Lys Asp Gly Arg Tyr Glu Glu Ser Leu Ala
    210                 215                 220
Ile Ile Arg Gln Arg Thr Ala Leu Ala Gly Val Leu Gly Arg Val Cys
225                 230                 235                 240
Val His Pro Cys Glu Glu Asn Cys Arg Arg Gly Asn Val Asp Glu Pro
                245                 250                 255
Leu Ala Ile Arg Gly Leu Lys Arg Phe Val Ala Asp Tyr Glu Val Lys
                260                 265                 270
Arg Gly Arg Arg Pro Val Ala Val Cys Gly Gly Asn Leu Phe Thr Gly
                275                 280                 285
Pro Trp Arg Pro Ala Gly Gln Ala Gly Gly Glu Thr Thr Ala Val
    290                 295                 300
Thr Ser Gly Lys Lys Val Ala Ile Ile Gly Ala Gly Pro Ala Gly Leu
305                 310                 315                 320
Ser Ala Ala Tyr Gln Leu Ala Gly Arg Gly Tyr Lys Val Thr Ile Phe
                325                 330                 335
Glu Ala Leu Pro Val Ala Gly Gly Met Leu Ala Val Gly Ile Pro Ser
                340                 345                 350
Tyr Arg Leu Pro Arg Asp Ile Leu Ala Gly Glu Ile Glu Ala Ile Lys
                355                 360                 365
Ala Leu Gly Val Thr Ile Asn Leu Asn Thr Arg Val Gly Val Asp Val
                370                 375                 380
Thr Met Asp Gln Leu Gln Arg Asp Tyr Asp Ala Val Phe Ile Ala Thr
385                 390                 395                 400
Gly Leu His Ala Ser Ser Arg Met Gly Val Ala Gly Glu Asp Glu Gly
                405                 410                 415
Tyr Gly Gly Phe Ile Pro Gly Val Lys Phe Leu Arg Asp Leu Asn Leu
                420                 425                 430
```

```
Asp Arg Cys Pro Ser Leu Glu Gly Lys Val Val Ala Val Val Gly Gly
        435                 440                 445

Gly Asn Val Ala Met Asp Cys Ala Arg Ser Ala Leu Arg Arg Gly Ala
    450                 455                 460

Arg Glu Val His Leu Ile Tyr Arg Arg Ser Arg Ala Glu Met Pro Ala
465                 470                 475                 480

His Ala Thr Glu Val Arg Asp Ala Glu Ala Glu Gly Val Ile Tyr His
                485                 490                 495

Phe Leu Val Asn Pro Thr Ala Leu Val Ala Glu Lys Gly Asn Ile Lys
            500                 505                 510

Gly Met Gln Cys Val Arg Met Lys Leu Gly Glu Pro Asp Asp Ser Gly
            515                 520                 525

Arg Arg Arg Pro Val Pro Val Pro Gly Thr Glu Phe Phe Leu Pro Cys
        530                 535                 540

Asp Ile Val Val Pro Ala Ile Gly Gln Ala Ala Asp Leu Ser Phe Leu
545                 550                 555                 560

Asp Gly Arg Ile Glu Val Gly Lys Arg Gly Thr Ile Ser Val Asp Pro
                565                 570                 575

Val Thr Leu Ala Thr Ser Val Pro Gly Val Phe Ala Gly Gly Asp Ile
            580                 585                 590

Val Leu Gly Ala Arg Thr Val Val Glu Ala Val Ala Gln Gly Asn Arg
            595                 600                 605

Ala Ala Val Ser Ile Asp Gln Tyr Leu Arg Gln Gly Thr Thr Ser Pro
        610                 615                 620

Thr Val Glu Asp Glu Leu Asp Ala Trp Leu Glu Lys Val Gly Val Tyr
625                 630                 635                 640

Asp Pro Glu Glu Asp Val Gly Ile Tyr Gly Gly Arg Pro Arg Gln Ala
                645                 650                 655

Glu Arg Val Ala Pro Leu Ala Glu Arg Val Lys Asp Phe Arg Glu Val
                660                 665                 670

Glu Gly Gly Phe Asp Phe Tyr Ala Gly Arg Ala Glu Ala Glu Arg Cys
            675                 680                 685

Leu Arg Cys Tyr Arg Val Gly Met Met Val Leu Ala Gly Glu Gly Glu
    690                 695                 700

Ser Asn Gly
705
```

UNITED STATES PATENT AND TRADEMARK OFFICE
CERTIFICATE OF CORRECTION

PATENT NO.         : 10,377,994 B2
APPLICATION NO.    : 16/162427
DATED              : August 13, 2019
INVENTOR(S)        : Arren Bar-Even et al.

Page 1 of 1

It is certified that error appears in the above-identified patent and that said Letters Patent is hereby corrected as shown below:

On the Title Page

Item (73) Assignee, Line 1:
"Developmetn" should be changed to -- Development --

Signed and Sealed this
Nineteenth Day of November, 2019

Andrei Iancu
*Director of the United States Patent and Trademark Office*